United States Patent
Gasser et al.

(10) Patent No.: US 9,598,451 B2
(45) Date of Patent: Mar. 21, 2017

(54) BIS-ORGANOMETALLIC 2-AMINO-3-HYDROXY-2-METHYLPROPANENITRILE DERIVATIVES FOR USE AS ANTHELMINTICS

(71) Applicants: UNIVERSITÄT ZÜRICH, Zürich (CH); THE UNIVERSITY OF MELBOURNE, Melbourne, Victoria (AU)

(72) Inventors: Gilles Gasser, Zug (CH); Robin B. Gasser, Werribee (AU); Jeannine Hess, Oberkirch (CH); Abdul Jabbar, Tarneit (AU); Malay Patra, Cambridge, MA (US)

(73) Assignees: UNIVERSITÄT ZÜRICH, Zürich (CH); THE UNIVERSITY OF MELBOURNE, Melbourne, Victoria (AU)

( * ) Notice: Subject to any disclaimer, the term of this patent is extended or adjusted under 35 U.S.C. 154(b) by 0 days.

(21) Appl. No.: 15/023,413

(22) PCT Filed: Sep. 26, 2014

(86) PCT No.: PCT/EP2014/070708
§ 371 (c)(1),
(2) Date: Mar. 21, 2016

(87) PCT Pub. No.: WO2015/044396
PCT Pub. Date: Apr. 2, 2015

(65) Prior Publication Data
US 2016/0215009 A1    Jul. 28, 2016

(30) Foreign Application Priority Data
Sep. 26, 2013 (EP) .................................. 13186260

(51) Int. Cl.
C07F 17/02 (2006.01)
A01N 55/02 (2006.01)

(52) U.S. Cl.
CPC .............. *C07F 17/02* (2013.01); *A01N 55/02* (2013.01)

(58) Field of Classification Search
CPC .................................. C07F 17/02; A01N 55/02
USPC .......................................................... 556/136
See application file for complete search history.

(56) References Cited

FOREIGN PATENT DOCUMENTS

| WO | 2005/044784 | | 5/2005 | |
|----|-------------|---|--------|---|
| WO | WO 2005044784 A1 | * | 5/2005 | ............. A01N 37/46 |
| WO | 2008/062005 | | 5/2008 | |

* cited by examiner

*Primary Examiner* — Porfirio Nazario Gonzalez
*Assistant Examiner* — Kofi Adzamli
(74) *Attorney, Agent, or Firm* — Soroker Agmon Nordman

(57) ABSTRACT

The invention comprises a compound characterized by a general formula (1),

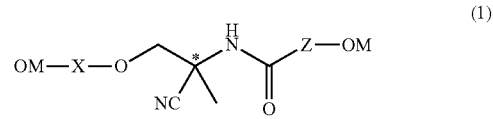

wherein X is a group described by a general formula —$K_p$—$F_l$—$K_q$—, wherein
$F_l$ is —C(=O)—, —C(=S)—, with l being 0 or 1,
$K_p$ is a $C_p$-alkyl with p being 0, 1, 2, 3 or 4,
$K_q$ is a $C_q$-alkyl with q being 0, 1, 2, 3 or 4, and
wherein Z is a group described by a general formula —$K_r$—$F_i$—$K_t$—, wherein
$F_i$ —O—, —S—, —O—C(=O)—, —O—C(=S)—, —S—C(=O)— or —NH—(C=O)— with i being 0 or 1,
$K_r$ is a $C_r$-alkyl with r being 0, 1, 2, 3 or 4,
$K_t$ is a $C_t$-alkyl with t being 0, 1, 2, 3 or 4,
wherein each OM is an organometallic compound independently selected from each other from the group of an unsubstituted or substituted metal sandwich compound, an unsubstituted or substituted half metal sandwich compound or a metal carbonyl compound and their use.

17 Claims, 3 Drawing Sheets

BIS-ORGANOMETALLIC 2-AMINO-3-HYDROXY-2-METHYLPROPANENITRILE DERIVATIVES FOR USE AS ANTHELMINTICS

RELATED APPLICATIONS

The present application claims priority as a US national phase under 35 U.S.C. 363 of PCT/EP2014/070708 filed on Sep. 26, 2014, which claims priority from patent application Ser. No. 13/186,260.9 filed in Europe on Sep. 26, 2013, the disclosures of which are incorporated herein by reference.

FIELD OF THE INVENTION

The present invention relates to bis-organometallic 2-amino-3-hydroxy-2-methylpropanenitrile derivatives and their use as anthelmintics.

BACKGROUND OF THE INVENTION

Parasites cause significant economic losses to agriculture worldwide due to poor productivity, limited growth rates and death. According to some estimates, the financial damage caused by parasites to the livestock industry is in the order of tens of billions of dollars per annum. Decreased productivity influences not only the livestock industry but also substantially affects global food production. Moreover, in spite of the anthelmintic drugs discovered and marketed in the last decades, problems of parasitic worms persist and multi-drug resistance to most classes of anthelmintics is widespread. The development of new classes of anthelmintics is a major priority. Any anthelmintic developed for parasites of livestock would also have application to parasites of humans and other animals, including companion animals, such as dogs, cats and equids. One sixth of the human population in earth is affected chronically by at least one parasitic helminth, and the socioeconomic burden (in DALYs) is greater than that of cancer and diabetes. Some helminths, such as *Schistosoma haematobium*, *Opistorchis viverrini* and *Clonorchis sinensis* induce malignant cancers in humans.

Recently, a new class of synthetic anthelmintics referred to as Amino-Acetonitrile Derivatives (AADs, see WO2005/044784A1), has been commercially developed under the trade name Zolvix® (also known as monepantel) for the treatment of infected sheep.

Monepantel (AAD 1566)

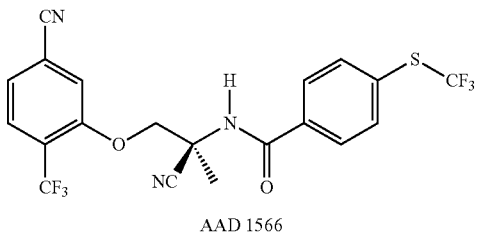

AAD 1566

The precise mode of action of monepantel is not yet elucidated, although an interaction of AADs with a specific acetylcholine receptor (nAChR) subunit has been proposed. This target is only present in nematodes but not in mammals, making it relevant for the development of a new class of anthelmintic drugs. Of high importance, a mutant of *Haemonchus contortus* with a reduced sensitivity to monepantel was recently identified using a novel in vitro selection procedure (L. Rufener, R. Baur, R. Kaminsky, P. Maeser and E. Sigel, Mol. Pharmacol., 2010, 78, 895-902), indicating that resistance will develop in gastrointestinal nematodes of livestock. This observation has been noticed for all current anthelmintics on the market. In light of the above referenced state of the art, the objective of the present invention is to provide novel compounds to control parasites of human beings and livestock.

This objective is attained by the subject-matter of the independent claims.

SUMMARY OF THE INVENTION

According to a first aspect of the invention provided herein are organometallic compounds characterized by a general formula (1),

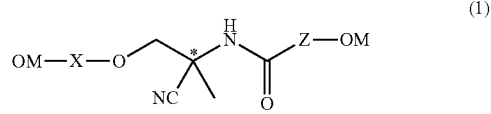

(1)

wherein X is a group described by a general formula —$K_p$—$F_l$—$K_q$—, wherein
$F_l$ is —C(=O)—, —C(=S)—, with l being 0 or 1,
$K_p$ is a $C_p$-alkyl with p being 0, 1, 2, 3 or 4,
$K_q$ is a $C_q$-alkyl with q being 0, 1, 2, 3 or 4, and
wherein Z is a group described by a general formula —$K_r$—$F_i$—$K_t$—, wherein
$F_i$ is —O—, —S—, —O—C(=O)—, —O—C(=S)—, or —NH—(C=O)— with i being 0 or 1,
$K_r$ is a $C_r$-alkyl with r being 0, 1, 2, 3 or 4,
$K_t$ is a $C_t$-alkyl with t being 0, 1, 2, 3 or 4,
wherein OM is an organometallic compound independently selected from the group of an unsubstituted or substituted metal sandwich compound, an unsubstituted or substituted half metal sandwich compound or a metal carbonyl compound, The term "substituted" refers to the addition of a substituent group to a parent compound.

"Substituent groups" can be protected or unprotected and can be added to one available site or to many available sites in a parent compound. Substituent groups may also be further substituted with other substituent groups and may be attached directly or by a linking group such as an alkyl, an amide or hydrocarbyl group to a parent compound, "Substituent groups" amenable herein include, without limitation, halogen, oxygen, nitrogen, sulphur, hydroxyl, alkyl, alkenyl, alkynyl, acyl (—(O)$R^a$), carboxyl (—C(O)O$R^a$), aliphatic groups, alicyclic groups, alkoxy, substituted oxy (—O$R^a$), aryl, aralkyl, heterocyclic radical, heteroaryl, heteroarylalkyl, amino (—N($R^b$)($R^c$)), imino (=N$R^b$), amido (—C(O)N($R^b$)($R^c$) or —N($R^b$)C(O)$R^a$), hydrazine derivates (—C(NH)NR$^a$R$^B$), tetrazole (—CN$_4$H$_2$), azido (—N$_3$), nitro (—NO$_2$), cyano (—CN), isocyano (—NC), cyanato (—OCN), isocyanato (—NCO), thiocyanato (—SCN); isothiocyanato (—NCS); carbamido (—OC(O)N($R^b$)($R^c$) or —N($R^b$)C(O)($R^a$), thiol (—S$R^b$), sulfinyl (—S(O)$R^b$), sulfonyl (—S(O)$_2R^b$), sulfonamidyl (—S(O)$_2$N($R^b$)($R^c$)or —N($R^b$)S(O)$_2R^b$) and fluorinated compounds —CF$_3$, —OCF$_3$, —SCF$_3$, —SOCF$_3$ or —SO$_2$CF$_3$. Wherein each $R^a$, $R^b$ and $R^c$ is, independently, H or a further substituent group with a preferred list including without limitation, H, alkyl, alkenyl, alkynyl, aliphatic, alkoxy, acyl, aryl, heteroaryl, alicyclic, heterocyclic and heteroarylalkyl.

As used herein the term "alkyl," refers to a saturated straight or branched hydrocarbon moiety containing up to 10, particularly up to 4 carbon atoms. Examples of alkyl groups include, without limitation, methyl, ethyl, propyl, butyl, isopropyl, n-hexyl, octyl, decyl and the like. Alkyl groups typically include from 1 to about 10 carbon atoms ($C_1$-$C_{10}$ alkyl), particularly with from 1 to about 4 carbon atoms ($C_1$-$C_4$ alkyl). The term "cycloalkyl" refers to an interconnected alkyl group forming a ring structure. Alkyl or cycloalkyl groups as used herein may optionally include further substituent groups. Examples for a substituted alkyl group (e.g. a substituted —$CH_3$ or a substituted —$CH_2CH_3$) may be —$CHF_2$ or —$CH_2CH_2F$, thus, comprising additional fluorides as substituents.

As used herein the term "alkenyl," refers to a straight or branched hydrocarbon chain moiety containing up to 10 carbon atoms and having at least one carbon-carbon double bond. Examples of alkenyl groups include, without limitation, ethenyl, propenyl, butenyl, 1-methyl-2-buten-1-yl, dienes such as 1,3-butadiene and the like. Alkenyl groups typically include from 2 to about 10 carbon atoms, more typically from 2 to about 4 carbon atoms. Alkenyl groups as used herein may optionally include further substituent groups.

As used herein the term "alkynyl," refers to a straight or branched hydrocarbon moiety containing up to 10 carbon atoms and having at least one carbon-carbon triple bond. Examples of alkynyl groups include, without limitation, ethynyl, 1-propynyl, 1-butynyl, and the like. Alkynyl groups typically include from 2 to about 10 carbon atoms, more typically from 2 to about 4 carbon atoms. Alkynyl groups as used herein may optionally include further substituent groups.

As used herein the term "alkoxy," refers to an oxygen-alkyl moiety, wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. The term "cycloalkoxy" refers to an interconnected alkoxy group forming a ring structure. Alkoxy or cycloalkoxy groups as used herein may optionally include further substituent groups. One example for a substituted alkoxy group (e.g. —$OCH_3$) may be —$OCF_3$, thus, comprising three additional substituents (namely fluorides).

As used herein the term "aryl" refers to a hydrocarbon with alternating double and single bonds between the carbon atoms forming a ring structure (in the following an "aromatic hydrocarbon"). The term "heteroaryl" refers to aryl compounds in which at least one carbon atom is replaced with an oxygen, a nitrogen or a sulphur atom. The aromatic hydrocarbon may be neutral or charged. Examples of aryl or hetero aryl groups are benzene, pyridine, pyrrole or cyclopenta-1,3-diene-anion. Aryl or hetero aryl groups as used herein may optionally include further substituent groups.

As used herein the term "organometallic compound" refers to a compound comprising at least one metal, in particular at least one transition metal (a metal selected from the group 3 to group 12 metals of the periodic table), as well as at least one metal-carbon bond.

As used herein the term "metal sandwich compound" refers to a compound comprising a metal, in particular a transition metal, bound to two aryl or heteroaryl ligands (in the following "sandwich ligands") by a haptic covalent bound. It may comprise a cationic metal sandwich complex, e.g. cobaltocenium with a suitable counter anion such as iodide, chloride, bromide, fluoride, triflate, tetraborofluoride, hexafluorophosphate. The aryl or heteroaryl ligands may be unsubstituted or substituted.

As used herein the term "half metal sandwich compound" refers to a compound comprising a metal, in particular a transition metal, bound to just one aryl or heteroaryl ligand (sandwich ligand). The other ligand may comprise—without being limited to—alkyl, allyl, CN or CO, in particular CO.

As used herein the term "metal carbonyl compound" refers to a coordination complex of at least one transition metal with a carbon monoxide (CO) ligand. It may comprise a neutral, anionic or cationic complex. The carbon monoxide ligand may be bond terminally to a single metal atom or may be bridging to two or more metal atoms. The complex may be homoeleptic (containing only carbon monoxide ligands) or heteroeleptic.

As used herein the term "metallocene" refers to a metal sandwich compound comprising an aryl or heteroaryl five ring ligand (in the following "cp-ligand" or "hetero cp-ligand").

In some embodiments, one organometallic compound may be attached directly to the —O—C— moiety of the parent compound (e.g. OM—O—C—) with l, q and p being 0. In some embodiments, one organometallic compound may be connected by a $C_1$-to $C_4$-alkyl to the —O—C— moiety of the parent compound (e.g. OM—$CH_2$—O—C—) with l and q being 0 and p being an integer of 1 to 4, in particular p being 1. In some embodiments, one organometallic compound may be connected to the —O—C— moiety of the parent compound by a —C(=O)— or —C(=S)— group, in particular by a —C(=O)— group, with l being 1, q and p being 0 (e.g. OM—C(=O)—O—C—). In some embodiments, one organometallic compound may be connected to the —O—C— moiety of the parent compound by a —C(=O)— or —C(=S)—group, in particular by a —C(=O)— group, with l being 1, q being 0 and p being an integer of 1 to 4, in particular p being 1 (e.g. OM—$CH_2$—C(=O)—O—C—). In some embodiments, one organometallic compound may be connected to the —O—C— moiety of the parent compound by a —C(=O)— or —C(=S)— group, in particular by a —C(=O)— group, with l being 1, p being 0 and q being an integer of 1 to 4, in particular q being 1 (e.g. OM—C(=O)—$CH_2$—O—C—). In some embodiments, the organometallic compound may be attached directly to the —(NH)C=O— moiety of the parent compound (e.g. —(NH)C=O—OM) with i, r and t being 0. In some embodiments, the organometallic compound may be connected by a $C_{1-4}$-alkyl to the —(NH)C=O— moiety of the parent compound with i and t being 0 and r being an integer of 1 to 4, in particular r being 1 (e.g. —(NH)C=O—$CH_2$—OM). In some embodiments, the organometallic compound may be connected to the —(NH)C=O— moiety of the parent compound by a $C_{1-4}$-alkyl-O—, —$C_{1-4}$-alkyl-S—, —$C_{1-4}$-alkyl-O—C(=O)—, —$C_{1-4}$-alkyl-O—C(=S)—, —$C_{1-4}$alkyl-S—C(=O)— or —$C_{1-4}$-alkyl-NH—(C=O)— group, with i being 1, r being an integer of 1 to 4, in particular r being 1, and t being 0 (e.g. —(NH)C=O—$CH_2$—O—C(=O)—OM, —(NH)C=O—$CH_2$—$CH_2$—O—OM or —(NH)C=O—$CH_2$NH—(C=O)—OM). In some embodiments, the organometallic compound may be connected to the —(NH)C=O— moiety of the parent compound by a —$C_{1-4}$alkylalkyl or alkylalkyl group, with i being 1, r and t being an integer of 1 to 4 (e.g. —(NH)C=O—$CH_2$—O—C(=O)—$CH_2$—$CH_2$—OM).

In some embodiments, i of $F_i$, r of $K_r$ and t of $K_t$ are 0.
In some embodiments, l of $F_l$ is 0.

In some embodiments, $F_l$ is —C(=O)— or —C(=S) with l being 1. In some embodiments, $F_l$ is —C(=O)— with l being 1.

In some embodiments, l of $F_l$ is 0, wherein q of $K_q$ and p of $K_p$ are 0.

In some embodiments, $F_l$ is —C(=O)— or —C(=S), with l being 1, wherein q of $K_q$ and p of $K_p$ are 0. In some embodiments, $F_l$ is —C(=O)—, with l being 1, wherein q of $K_q$ and p of $K_p$ are 0.

In some embodiments, $F_l$ is —C(=O)—, with l being 1, q of $K_q$ is 0 and is $C_1$-alkyl. In some embodiments, $F_l$ is —C(=O)—, with l being 1, q of $K_q$ is 0 and $K_p$ is $C_2$-alkyl.

In some embodiments, l of $F_l$ is 0, q of $K_q$ is 0 and $K_p$ is $C_1$-alkyl. In some embodiments, l of $F_l$ is 0, q of $K_q$ is 0 and $K_p$ is $C_2$-alkyl.

In some embodiments, $F_l$ is —C(=O)—, with l being 1, p of $K_p$ is 0 and $K_q$ is $C_1$-alkyl. In some embodiments, $F_l$ is —C(=O)—, with l being 1, p of $K_p$ is 0 and $K_q$ is $C_2$-alkyl.

In some embodiments, $F_l$ is —C(=O)—, with l being 1, $K_p$ is $C_1$-alkyl and $K_q$ is $C_1$-alkyl or $C_2$-alkyl. In some embodiments, $F_l$ is —C(=O)—, with l being 1, $K_p$ is $C_2$-alkyl and $K_q$ is $C_1$-alkyl or $C_2$-alkyl.

In some embodiments, i of $F_i$, r of $K_r$ and t of $K_t$ are 0 and l of $F_l$ is 0.

$F_l$ is —(=O)— or —C(=S) with l being 1, $F_l$ is —C(=O)— with l being 1, l of $F_l$ is 0, wherein q of $K_q$ and p of $K_p$ are 0, $F_l$ —C(=O)— or —C(=S), with l being 1, wherein q of $K_q$ and p of $K_p$ are 0, $F_l$ is —C(=O)—, with l being 1, wherein q of $K_q$ and p of $K_p$ are 0, $F_l$ is —C(=O)—, with l being 1, q of $K_q$ is 0 and $K_p$ is $C_1$-alkyl, $F_l$ is —C(=O)—, with l being 1, q of $K_q$ is 0 and $K_p$ is $C_2$-alkyl, $F_l$ is —C(=O)—, with l being 1, $K_p$ is $C_1$-alkyl and $K_q$ is $C_1$-alkyl or $C_2$-alkyl, $F_l$ —C(=O)—, with l being 1, $K_p$ is $C_2$-alkyl and is $C_1$-alkyl or $C_2$-alky, $F_l$ is —C(=O)—, with l being 1, p of $K_p$ is 0 and $K_q$ is $C_1$-alkyl, $F_l$ is —C(=O)—, with l being 1, p of $K_p$ is 0 and $K_q$ is $C_2$-alkyl, l of $F_l$ is 0, q of $K_q$ is 0 and $K_p$ is $C_1$-alkyl, or l of $F_l$ is 0, q of $K_q$ is 0 and $K_p$ is $C_2$-alkyl.

In some embodiments, at least one OM is a metal sandwich complex, wherein each of the two sandwich ligands is selected independently from a five-membered or six-membered aryl group or a five-membered or six-membered heteroaryl group. In some embodiments, at least one OM is a metal sandwich complex, wherein both sandwich ligands are the same and are selected from a five-membered or six-membered aryl group or a five-membered or six-membered heteroaryl group. In some embodiments, at least one OM is a metal sandwich complex, wherein at least one of the two ligands is selected from a five-membered or six-membered aryl group, wherein the other is selected from a five-membered or six-membered heteroaryl group. In some embodiments, at least one OM is a substituted or unsubstituted metallocene, wherein each of two ligands is selected independently from a five-membered aryl group (cp-ligand) or a five-membered heteroaryl group (hetero cp-ligand). The metal sandwich complex may be connected to the parent molecule by any atom of one of the two sandwich ligands Furthermore or additionally, it may comprise a cationic metal sandwich complex, e.g. cobaltocenium with a suitable counter anion such as iodide, chloride bromide, fluoride, triflate, tetrafluoroborate or hexafluorophosphate.

In some embodiments, both OM are the same.

In some embodiments, OM is a metal sandwich complex of the general formula (2a),

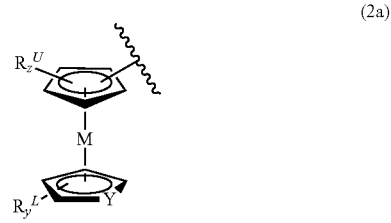

(2a)

wherein M is a metal selected from the group of Fe, Ru, Co, Ni, Cr, Os or Mn, and Y is C or N, and z of $R_z^U$ is 0, 1, 2, 3 or 4, and y of $R_y^L$ is 0, 1, 2, 3, 4 or 5 and each $R^L$ and each $R^U$ are independently from any other $R^L$ and $R^U$ selected from an unsubstituted or substituted $C_1$-$C_{10}$ alkyl, an unsubstituted or substituted $C_1$-$C_{10}$ alkenyl, an unsubstituted or substituted $C_1$-$C_{10}$ alkynyl, an unsubstituted or substituted $C_3$-$C_8$ cycloalkyl, an unsubstituted or substituted $C_1$-$C_{10}$ alkoxy, an unsubstituted or substituted $C_3$-$C_8$ cycloalkoxy, an unsubstituted or substituted $C_6$-$C_{14}$ aryl, an unsubstituted or substituted 5- to 10-membered heteroaryl, wherein 1 to 4 ring atoms are independently selected from nitrogen, oxygen or sulfur, an unsubstituted or substituted 5- to 10-membered heteroalicyclic ring, wherein 1 to 3 ring atoms are independently selected from nitrogen, oxygen or sulfur, —$OR^3$, —$SR^3$, —$C(O)R^3$, —$C(S)R^3$, —$C(O)OR^3$, —$C(S)OR^3$, —$C(O)SR^3$, —$C(O)NR^3R^4$, —$NR^3R^4$, —$S(O)_2R^3$, —$S(O)_2NR^3R^4$, —$SCF_3$, —$SOCF_3$ or —$SO_2CF_3$, or —$OCF_3$, —CN, —$CF_3$, —SCN, —F, —Cl, —Br or —I wherein $R^3$ and $R^4$ are independently selected from the group consisting of hydrogen, unsubstituted or substituted $C_1$-$C_4$ alkyl, in particular a substituted $C_1$-$C_4$ alkyl, and $C_1$-$C_4$ alkyl substituted with $C_1$-$C_4$ alkoxy.

In some embodiments, z of $R_z^U$ is 0, 1, 2, 3 or 4, and y of $R_y^L$ is 0, 1, 2, 3, 4 or 5, and each R and each $R^U$ are independently from any other $R^L$ and $R^U$ selected from —$OR^3$, —$SR^3$, —$C(O)R^3$, —$C(S)R^3$, —$C(O)OR^3$, —$C(S)OR^3$, —$C(O)SR^3$, —$C(O)NR^3R^4$, —$S(O)_2R^3$, —$S(O)_2OR^3$, —$S(O)_2NR^3R^4$, —$SCF_3$, —$SOCF_3$, —$SO_2CF_3$, —$OCF_3$, —CN, —$CF_3$, —SCN, —F, —Cl, —Br or —I, in particular from —$OCF_3$, —$C(O)R^3$, —$C(S)R^3$, —$C(O)OR^3$, —$C(S)SR^3$, —$C(O)NR^3R^4$, —$SCF_3$, —$SOCF_3$ or —$SO_2CF_3$, wherein $R^3$ and $R^4$ are independently selected from the group consisting of hydrogen, unsubstituted or substituted $C_1C_4$ alkyl, and $C_1$-$C_4$ alkyl substituted with $C_1$-$C_4$ alkoxy.

In some embodiments, z of $R_z^U$ is 0, 1, 2, 3 or 4, and y of $R_y^L$ is 0, 1, 2, 3, 4 or 5, and each $R^L$ and each $R^U$ are independently from any other $R^L$ and $R^U$ selected from —$OCF_3$, —$SCF_3$, —$SOCF_3$ or —$SO_2CF_3$, in particular from —$SCF_3$, —$SOCF_3$ or —$SO_2CF_3$, wherein $R^3$ and $R^4$ are independently selected from the group consisting of hydrogen, unsubstituted or substituted $C_1$-$C_4$ alkyl, and $C_1$-$C_4$ alkyl substituted with $C_1$-$C_4$ alkoxy.

In some embodiments, M of the general formula 2a is Fe, Ru or Co. In some embodiments, M of the general formula 2a is Fe or Ru. In some embodiments, M of the general formula 2a is Fe.

In some embodiments, Y is C.

In some embodiments, M of the general formula 2a is Fe and Y is C.

In some embodiments, Y is C, and z of $R_z^U$ is 0, 1, 2, 3 or 4, y of $R_y^L$ is 0, 1, 2, 3, 4 or 5, and each $R^L$ and each $R^U$ are independently from any other $R^L$ and $R^U$ selected from $-OR^3$, $-SR^3$, $-C(O)R^3$, $-C(S)R^3$, $-C(O)OR^3$, $-C(O)SR^3$, $-C(O)NR^3R^4$, $-S(O)_2R^3$, $-S(O)_2OR^3$, $-S(O)_2NR^3R^4$, $-SCF_3$, $-SOCF_3$, $-SO_2CF_3$, $-OCF_3$, $-CN$, $-CF_3$, $-SCN$, $-F$, $-Cl$, $-Br$ or $-I$, in particular from $-OCF_3$, $-C(O)R^3$, $-C(S)R^3$ $-C(O)OR^3$, $-C(S)OR^3$, $-C(O)SR^3$, $-C(O)NR^3R^4$, $-SCF_3$, $-SOCF_3$ or $-SO_2CF_3$, wherein $R_3$ and $R^4$ and are independently selected from the group consisting of hydrogen, unsubstituted or substituted $C_1$-$C_4$ alkyl, and $C_1$-$C_4$ alkyl substituted with $C_1$-$C_4$ alkoxy.

In some embodiments, z of $R_z^U$ is 1 and y of $R_y^L$ is 0 and $R^U$ is situated on the neighboring carbon atom of the cp-ligand with respect to the attachment position of the organometallic moiety (yielding a 1,2 substitution pattern on the cp-ligand).

In some embodiments, Y is C, and z of $R_z^U$ is 0, 1, 2, 3 or 4, y of $R_y^L$ is 0, 1, 2, 3, 4 or 5, and each $R^L$ and each $R^U$ are independently from any other $R^L$ and $R^U$ selected from $-SCF_3$, $-SOCF_3$ or $-SO_2CF_3$, wherein $R^3$ and $R^4$ are independently selected from the group consisting of hydrogen, unsubstituted or substituted $C_1$-$C_4$ alkyl, and $C_1C_4$ alkyl substituted with $C_1$-$C_4$ alkoxy.

In some embodiments, M of the general formula 2a is a metal selected from the group of Fe, Ru, Co, Ni, Cr, Os or Mn, in particular M is Fe, Y is C or N, z of $R_z^U$ is 1, y of $R_y^L$ is 1, and wherein $R^U$ and $R^L$ are selected independently from any other $R^U$ and $R^L$ from $-OR^3$, $-SR^3$, $-C(O)R^3$, $-C(S)R^3$ $-C(O)OR^3$, $-C(O)OR^3$, $-C(S)OR^3$, $-C(O)SR^3$ $-C(O)NR^3R^4$, $-NR^3R^4$, $-S(O)_2R^3$, $-S(O)_2OR^3$, $-S(O)_2NR^3R^4$, $-SCF_3$, $-SOCF_3$, $-SO_2CF_3$, $-OCF_3$, $-CN$, $-CF_3$, $-SCN$, $-F$, $-Cl$, $-BR$ or $-I$, in particular from $-OCF_3$, $-C(O)R^3$, $-C(S)R^3$, $-C(O)OR^3$, $-C(S)OR^3$, $-C(O)SR^3$, $-C(O)NR^3R^4$, $-SCF_3$, $-SOCF_3$ or $SO_2CF_3$, more particularly from $-SCF_3$, $-SOCF_3$ or $-SO_2CF_3$, wherein $R^3$ and $R^4$ are independently selected from the group consisting of hydrogen, unsubstituted or substituted $C_1$-$C_4$ alkyl, and $C_1$-$C_4$ alkyl substituted with $C_1$-$C_4$ alkoxy.

In some embodiments, M of the general formula 2a is a metal selected from the group of Fe, Ru, Co, Ni, Cr, Os or Mn, in particular M is Fe or Ru, more particularly M is Fe, Y is C or N, and z of $R_z^U$ is 1, y of $R_y^L$ is 0, and wherein $R^U$ is selected from $-OR^3$, $-SR^3$, $-C(O)R^3$, $-C(S)R^3$ $-C(O)OR^3$, $-C(S)OR^3$, $-C(O)SR^3$, $-C(O)NR^3R^4$, $-NR^3R^4$, $-S(O)_2R^3$, $-S(O)_2OR^3$, $-S(O)_2NR^3R^4$, $-SCF_3$, $-SOCF_3$, $-SO_2CF_3$, $-OCF_3$, $-CN$, $-CF_3$, $-SCN$, $-F$, $-Cl$, $-Br$ or $-I$, in particular from $-OCF_3$, $-C(O)R^3$, $-C(S)R^3$ $-C(O)OR^3$, $-C(S)OR^3$, $-C(O)SR^3$, $-C(O)NR^3R^4$, $-SCF_3$, $-SOCF_3$ or $-SO_2CF_3$, more particularly from $-SCF_3$, $-SOCF_3$ or $-SO_2CF_3$, wherein $R^3$ and $R^4$ are independently selected from the group consisting of hydrogen, unsubstituted or substituted $C_1$-$C_4$ alkyl, and $C_1$-$C_4$ alkyl substituted with $C_1$-$C_4$ alkoxy.

In some embodiments, Y is C, and z of $R_z^U$ is 0, 1, 2, 3 or 4, y of $R_y^L$ is 0, 1, 2, 3, 4 or 5, and each $R^L$ and $R^U$ selected from $-OCF_3$, $-SCF_3$, $-SOCF_3$ or $-SO_2CF_3$, in particular from $-SCF_3$, $-SOCF_3$ or $-SO_2CF_3$.

In some embodiments, M of the general formula 2a is a metal selected from the group of Fe, Ru, Co, Ni, Cr, Os or Mn, in particular M is Fe or Ru, more particularly M is Fe, Y is C or N, z of $R_z^U$ is 1, y of $R_y^L$ is 1, and wherein $R^U$ and $R^L$ are selected independently from any other $R^U$ and $R^L$ from $-OCF_3$, $SCF_3$, $-SOCF_3$ or $-SO_2CF_3$, in particular from $-SCF_3$, $-SOCF_3$ or $-SO_2CF_3$, wherein in particular $R^U$ is situated on the neighboring carbon atom of the cp-ligand with respect to the attachment position of the organometallic moiety (yielding a 1,2 substitution pattern on the cp-ligand).

In some embodiments, M of the general formula 2a is a metal selected from the group of Fe, Ru, Co, Ni, Cr, Os or Mn, in particular M is Fe or Ru, more particularly M is Fe, Y is C or N, and z of $R_z^U$ 0, y of $R_y^L$ is 1 or 2, in particular z is 1, and wherein each $R^L$ is selected independently from any other $R^L$ from $-OCF_3$, $-SCF_3$, $-SOCF_3$ or $-SO_2CF_3$, in particular from $-SCF_3$, $-SOCF_3$ or $-SO_2CF_3$.

In some embodiments, M of the general formula 2a is a metal selected from the group of Fe, Ru, Co, Ni, Cr, Os or Mn, in particular M is Fe or Ru, more particularly M is Fe, Y is C or N, and z of $R_z^U$ is 1, y of $R_y^L$ is 0, and wherein $R^U$ is selected from $-OCF_3$, $-SCF_3$, $-SOCF_3$ or $-SO_2CF_3$, in particular from $-SCF_3$, $-SOCF_3$ or $-SO_2CF_3$, wherein in particular $R^U$ is situated on the neighboring carbon atom of the cp-ligand with respect to the attachment position of the organometallic moiety (yielding a 1,2 substitution pattern on the cp-ligand).

In some embodiments, Y is N, z of $R_z^U$ is 0 and y of $R_y^L$ is 0. In some embodiments, Y is N, z of $R_z^U$ is 0, y of $R_y^L$ is 0, and M of the general formula 2a is selected from the group of Fe, Ru or Co, in particular M is Fe or Ru, more particularly M is Fe.

In some embodiments, Y is C, z of $R_z^U$ is 0 and y of $R_y^L$ is 0. In some embodiments, Y is C, z of $R_z^U$ is 0, y of $R_y^L$ is 0, and M of the general formula 2a is selected from the group of Fe, Ru or Co, in particular M is Fe or Ru, more particularly M is Fe.

In some embodiments, I of $F_I$ is 0, q of $K_q$ is 0, p of $K_p$ is 0, Y is C, z of $R_z^U$ is 0, y of $R_y^L$ is 0, and M of the general formula 2a is selected from the group of Fe, Ru, Co, Ni, Cr, Os or Mn in particular M is Fe or Ru, more particularly M is Fe.

In some embodiments, i of $F_i$ is 0, r of $K_r$ is 0, t of $K_t$ is 0, Y is C, z of $R_z^U$ is 0, y of $R_y^L$ is 0, and M of the general formula 2a is selected from the group of Fe, Ru, Co, Ni, Cr, Os or Mn, in particular M is Fe or Ru, more particularly M is Fe.

In some embodiments, I of $F_I$ is 0, q of $K_q$ is 0, p of $K_p$ is 0, i of $F_i$ is 0, r of $K_r$ is 0, t of $K_t$ is 0, Y is C, z of $R_z^U$ is 0, y of $R_y^L$ is 0, and M of the general formula 2a is selected from the group of Fe, Ru, Co, Ni, Cr, Os or Mn, in particular M is Fe or Ru, more particularly M is Fe.

In some embodiments, M of the general formula 2 a is selected from the group of Fe, Ru, Co, Ni, Cr, Os or Mn, in particular M is selected from Fe, Ru or Co, more particularly M is Fe or Ru, Y is C, z of $R_z^U$ is 0, y of $R_y^L$ is 0, i of $F_i$, r of $K_r$ and t of $K_t$ are 0, and $F_l$ is $-C(=O)-$ or $-C(=S)$, with l being 1, q of $K_q$ is 0, p of $K_p$ is 0;

$F_l$ is $-C(=O)-$, with l being 1, q of $K_q$ is 0, p of $K_p$ is 0;

$F_l$ is $-C(=O)-$ or $-C(=S)$, with l being 1, q of $K_q$ is 0, $K_p$ is $C_1$- or $C_2$-alkyl;

$F_l$ is $-C(=O)-$, with l being 1, q of $K_q$ is 0, $K_p$ is $C_1$- or $C_2$-alkyl;

$F_l$ is —C(=O)—, with l being 1, p of $K_p$ is 0, $K_q$ is $C_1$- or $C_2$-alkyl;

$F_l$ is —C(=O)—, with l being 1, $K_p$ is $C_1$- or $C_2$-alkyl, $K_q$ is $C_1$- or $C_2$-alkyl;

$F_l$ is —C(=O)—, with l being 1, q of $K_q$ is 0, $K_p$ is $C_1$-alkyl $F_l$ is —C(=O)—, with l being 1, q of $K_q$ is 0, $K_p$ is $C_2$-alkyl;

$F_l$ is —C(=O)—, with l being 1, p of $K_p$ is 0, $K_q$ is $C_1$-alkyl, $F_l$ is —C(=O)—, with l being 1, p of $K_p$ is 0, $K_q$ is $C_2$-alkyl.

In some embodiments, M of the general formula 2a is selected from the group of Fe, Ru, Co, Ni, Cr, Os or Mn, in particular M is selected from Fe, Ru or Co, more particularly M is Fe or Ru, Y is C, z of $R_z^U$ is 1, y of $R_y^L$ is 0, i of $F_i$, r of $K_r$ and t of $K_t$ are 0, and $F_l$ is —C(=O)— or —C(=S), with l being 1, q of $K_q$ is 0, p of $K_p$ is 0;

$F_l$ is —C(=O)—, with l being 1, q of $K_q$ is 0, p of $K_p$ is 0;

$F_l$ is —C(=O)— or —C(=S), with l being 1, q of $K_q$ is 0, $K_p$ is $C_1$- or $C_2$-alkyl;

$F_l$ is —C(=O)—, with l being 1, q of $K_q$ is 0, $K_p$ is $C_1$- or $C_2$-alkyl;

$F_l$ is —C(=O)—, with l being 1, p of $K_p$ is 0, $K_q$ is $C_1$- or $C_2$-alkyl;

$F_l$ is —C(=O)—, with l being 1, $K_p$ is $C_1$- or $C_2$-alkyl, $K_q$ is $C_1$- or $C_2$-alkyl;

$F_l$ is —C(=O)—, with l being 1, q of $K_q$ is 0, $K_p$ is $C_1$-alkyl;

$F_l$ is —C(=O)—, with l being 1, q of $K_q$ is 0, $K_p$ is $C_2$-alkyl;

$F_l$ is —C(=O)—, with l being 1, p of $K_p$ is 0, $K_q$ is $C_1$-alkyl, $F_l$ is —C(=O)—, with i being 1, p of $K_p$ is 0, $K_q$ is $C_2$-alkyl, wherein $R^U$ is selected from —OCF$_3$, —SCF$_3$, —SOCF$_3$ or —SO$_2$CF$_3$, in particular from —SCF$_3$, —SPCF$_3$ or —SO$_2$CF$_3$, wherein in particular —OCF$_3$, —SCF$_3$, —SOCF$_3$ or —SO$_2$CF$_3$, more particularly —SCF$_3$, —SOCF$_3$ or —SO$_2$CF$_3$, are situated on the neighboring carbon atom of the cp-ligand with respect to the attachment position of the organometallic moiety (yielding a 1,2 substitution pattern on the cp-ligand).

In some embodiments, M of the general formula 2a is Fe, Y is C, z of $R_z^U$ is 0, y of $R_y^L$ is 0, i of $F_i$, r of $K_r$ and t of $K_t$ are 0, and $F_l$ is —C(=O)— or —C(=S), with l being 1, q of $K_q$ is 0, p of $K_p$ is 0;

$F_l$ is —C(=O)—, with l being 1, q of $K_q$ is 0, p of $K_p$ is 0;

$F_l$ is —C(=O)— or —C(=S), with l being 1, q of $K_q$ is 0, $K_p$ is $C_1$- or $C_2$-alkyl;

$F_l$ is —C(=O)—, with l being 1, q of $K_q$ is 0, $K_p$ is $C_1$- or $C_2$-alkyl;

$F_l$ is —C(=O)—, with l being 1, p of $K_p$ is 0, $K_q$ is $C_1$- or $C_2$-alkyl;

$F_l$ is —C(=O)—, with l being 1, $K_p$ is $C_1$- or $C_2$-alkyl, $K_q$ is $C_1$- or $C_2$-alkyl;

$F_l$ is —C(=O)—, with l being 1, q of $K_q$ is 0, $K_p$ is $C_1$-alkyl;

$F_l$ is —C(=O)—, with l being 1, q of $K_q$ is 0, $K_p$ is $C_2$-alkyl;

$F_l$ is —C(=O)—, with l being 1, p of $K_p$ is 0, $K_q$ is $C_1$-alkyl;

$F_l$ is —C(=O)—, with l being 1, p of $K_p$ is 0, $K_q$ is $C_1$-alkyl;

$F_l$ is —C(=O)—, with l being 1, p of $K_p$ is 0, $K_q$ is $C_2$-alkyl.

In some embodiments, M of the general formula 2a is Fe, Y is C, z of $R_z^U$ is 1, y of $R_y^L$ is 0, i of $F_i$, r of $K_r$ and t of $K_t$ are 0, and $F_l$ is —C(=O)— or —C(=O), with l being 1, q of $K_q$ is 0, p of $K_p$ is 0;

$F_l$ is —C(=O)—, with l being 1, q of $K_q$ is 0, p of $K_p$ is 0;

$F_l$ is —C(=O)— or —C(=S), with l being 1, q of $K_q$ is 0, $K_p$ is $C_1$- or $C_2$-alkyl;

$F_l$ is —C(=O)—, with l being 1, q of $K_q$ is 0, $K_p$ is $C_1$- or $C_2$-alkyl;

$F_l$ is —C(=O)—, with l being 1, p of $K_p$ is 0, $K_q$ is $C_1$- or $C_2$-alkyl;

$F_l$ is —C(=O)—, with l being 1, $K_p$ is $C_1$- or $C_2$-alkyl, $K_q$ is $C_1$- or $C_2$-alkyl;

$F_l$ is —C(=O)—, with l being 1, q of $K_q$ is 0, $K_p$ is $C_1$-alkyl;

$F_l$ is —C(=O)—, with l being 1, q of $K_q$ is 0, $K_p$ is $C_2$-alkyl;

$F_l$ is —C(=O)—, with l being 1, p of $K_p$ is 0, $K_q$ is $C_1$-alkyl; or $F_l$ is —C(=O)—, with l being 1, p of $K_p$ is 0, $K_q$ is $C_2$-alkyl.

wherein $R^U$ is selected from —OCF$_3$, —SCF$_3$, —SOCF$_3$ or —SO$_2$CF$_3$, in particular from —SCF$_3$, —SOCF$_3$ or —SO$_2$CF$_3$, wherein more particularly —OCF$_3$, —SCF$_3$, —SOCF$_3$ or —SO$_2$CF$_3$, in particular from —SCF$_3$, —SOCF$_3$ or —SO$_2$CF$_3$, are situated on the neighboring carbon atom of the cp-ligand with respect to the attachment position of the organometallic moiety (yielding a 1,2 substitution pattern on the cp-ligand)

In some embodiments, M of the general formula 2a is selected from the group of Fe, Ru, Co, Ni, Cr, Os or Mn, in particular M is selected Fe, Ru or Co, more particularly M is Fe or Ru, Y is C, z of $R_z^U$ is 0, y of $R_y^L$ is 0, and $F_l$ is —C(=O)— or —C(=O), with l being 1, q of $K_q$ is 0, p of $K_p$ is 0;

$F_l$ is —C(=O)—, with l being 1, q of $K_q$ is 0, p of $K_p$ is 0;

$F_l$ is —C(=O)— or —C(=S), with l being 1, q of $K_q$ is 0, $K_p$ is $C_1$- or $C_2$-alkyl;

$F_l$ is —C(=O)—, with l being 1, q of $K_q$ is 0, $K_p$ is $C_1$- or $C_2$-alkyl;

$F_l$ is —C(=O)—, with l being 1, p of $K_p$ is 0, $K_q$ is $C_1$- or $C_2$-alkyl;

$F_l$ is —C(=O)—, with l being 1, $K_p$ is $C_1$- or $C_2$-alkyl, $K_q$ is $C_1$- or $C_2$-alkyl;

$F_l$ is —C(=O)—, with l being 1, q of $K_q$ is 0, $K_p$ is $C_1$-alkyl $F_l$ is —C(=O)—, with l being 1, q of $K_q$ is 0, $K_p$ is $C_2$-alkyl;

$F_l$ is —C(=O)—, with l being 1, p of $K_p$ is 0, $K_q$ is $C_1$-alkyl, $F_l$ is —C(=O)—, with l being 1, p of $K_p$ is 0, $K_q$ is $C_2$-alkyl.

In some embodiments, M of the general formula 2a is selected from the group of Fe, Ru, Co, Ni, Cr, Os or Mn, in particular M is selected from Fe, Ru or Co, more particularly M is Fe or Ru, Y is C, z of $R_z^U$ is 1, y of $R_y^L$ is 0, and $F_l$ is —C(=O)— or —C(=S), with l being 1, q of $K_q$ is 0, p of $K_p$ is 0;

$F_l$ is —C(=O)—, with l being 1, q of $K_q$ is 0, p of $K_p$ is 0;

$F_l$ is —C(=O)— or —C(=S), with l being 1, q of $K_q$ is 0, $K_p$ is $C_1$- or $C_2$-alkyl;

$F_l$ is —C(=O)—, with l being 1, q of $K_q$ is 0, $K_p$ is $C_1$- or $C_2$-alkyl;

$F_l$ is —C(=O)—, with l being 1, p of $K_p$ is 0, $K_q$ is $C_1$- or $C_2$-alkyl;

$F_l$ is —C(=O)—, with l being 1, $K_p$ is $C_1$- or $C_2$-alkyl, $K_q$ is $C_1$- or $C_2$-alkyl;

$F_l$ is —C(=O)—, with l being 1, q of $K_q$ is 0, $K_p$ is $C_1$-alkyl $F_l$ is —C(=O)—, with l being 1, q of $K_q$ is 0, $K_p$ is $C_2$-alkyl, $F_l$ is —C(=O)—, with l being 1, p of $K_p$ is 0, $K_q$ is $C_1$-alkyl, $F_l$ is —C(=O)—, with l being 1, p of $K_p$ is 0, $K_q$ is $C_2$-alkyl.

wherein $R^U$ is selected from —OCF$_3$, —SCF$_3$, —SOCF$_3$ or —SO$_2$CF$_3$, in particular from —SCF$_3$, —SOCF$_3$ or —SO$_2$CF$_3$, wherein more particularly —OCF$_3$, —SCF$_3$, —SOCF$_3$ or —SO$_2$CF$_3$, in particular from —SCF$_3$, —SOCF$_3$ or —SO$_2$CF$_3$, are situated on the neighboring carbon atom of the cp-ligand with respect to the attachment position of the organometallic moiety (yielding a 1,2 substitution pattern on the cp-ligand).

In some embodiments, M of the general formula 2a is C, z of $R_z^U$ is 0, y of $R_y^L$ is 0, and $F_l$ is —C(=O)— or —C(=S), with l being 1, q of $K_q$ is 0, p of $K_p$ is 0;

$F_l$ is —C(=O)—, with l being 1, q of $K_q$ is 0, p of $K_p$ is 0;

$F_l$ is —C(=O)— or —C(=S), with l being 1, q of $K_q$ is 0, $K_p$ is $C_1$- or $C_2$-alkyl;

$F_l$ is —C(=O)—, with l being 1, q of $K_q$ is 0, $K_p$ is $C_1$- or $C_2$-alkyl;

$F_l$ is —C(=O)—, with l being 1, p of $K_p$ is 0, $K_q$ is $C_1$- or $C_2$-alkyl;

$F_l$ is —C(=O)—, with l being 1, $K_p$ is $C_1$- or $C_2$-alkyl, $K_q$ is $C_1$- or $C_2$-alkyl;

$F_l$ is —C(=O)—, with l being 1, q of $K_q$ is 0, $K_p$ is $C_1$-alkyl;

$F_l$ is —C(=O)—, with l being 1, q of $K_q$ is 0, $K_p$ is $C_2$-alkyl;

$F_l$ is —C(=O)—, with l being 1, p of $K_p$ is 0, $K_q$ is $C_1$-alkyl;

$F_l$ is —C(=O)—, with l being 1, p of $K_p$ is 0, $K_q$ is $C_2$-alkyl.

In some embodiments, M of the general formula 2a is Fe, Y is C, z of $R_z^U$ is 1, y of $R_y^L$ is 0, and $F_l$ is —C(=O)— or —C(=S), with l being 1, q of $K_q$ is 0, p of $K_p$ is 0;

$F_l$ is —C(=O)—, with l being 1, q of $K_q$ is 0, p of $K_p$ is 0;

$F_l$ is —C(=O)— or —C(=S), with l being 1, q of $K_q$ is 0, $K_p$ is $C_1$- or $C_2$-alkyl;

$F_l$ is —C(=O)—, with l being 1, q of $K_q$ is 0, $K_p$ is $C_1$- or $C_2$-alkyl;

$F_l$ is —C(=O)—, with l being 1, p of $K_p$ is 0, $K_q$ is $C_1$- or $C_2$-alkyl;

$F_l$ is —C(=O)—, with l being 1, $K_p$ is $C_1$- or $C_2$-alkyl, $K_q$ is $C_1$- or $C_2$-alkyl;

$F_l$ is —C(=O)—, with l being 1, q of $K_q$ is 0, $K_p$ is $C_1$-alkyl;

$F_l$ is —C(=O)—, with l being 1, q of $K_q$ is 0, $K_p$ is $C_2$-alkyl;

$F_l$ is —C(=O)—, with l being 1, p of $K_p$ is 0, $K_q$ is $C_1$-alkyl; or $F_l$ is —C(=O)—, with l being 1, p of $K_p$ is 0, $K_q$ is $C_2$-alkyl;

wherein $R^U$ is selected from —OCF$_3$, —SCF$_3$, —SOCF$_3$ or —SO$_2$CF$_3$, in particular from —SCF$_3$, —SOCF$_3$ or —SO$_2$CF$_3$, wherein more particularly —OCF$_3$, —SCF$_3$, —SOCF$_3$ or —SO$_2$CF$_3$, in particular from —SCF$_3$, —SOCF$_3$ or —SO$_2$CF$_3$, are situated on the neighboring carbon atom of the cp-ligand with respect to the attachment position of the organometallic moiety (yielding a 1,2 substitution pattern on the cp-ligand).

The metal sandwich complex of the general formula (2a) in the above mentioned embodiments may be neutral or cationic species, particularly the metal sandwich complex with M being Co may be in the cationic form comprising a counter anion CA selected from I$^-$, Cl$^-$, Br$^-$, F$^-$, BF$_4^-$, CF$_3$SO$_3^-$(OTf) or PF$_6^-$.

In some embodiments, OM is a half metal sandwich complex of the general formula (2b),

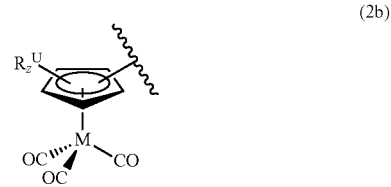

(2b)

wherein M is a metal selected from the group of Mn, Re or Tc, and z of $R_z^U$ is 0, 1, 2, 3 or 4, and each $R^U$ is independently from any other $R^U$ selected from an unsubstituted or substituted $C_1$-$C_{10}$ alkyl, an unsubstituted or substituted $C_1$-$C_{10}$ alkenyl, an unsubstituted or substituted $C_1$-$C_{10}$ alkynyl, an unsubstituted or substituted $C_3$-$C_8$ cycloalkyl, an unsubstituted or substituted $C_1$-$C_{10}$ alkoxy, an unsubstituted or substituted $C_3$-$C_8$ cycloalkoxy, an unsubstituted or substituted $C_6$-$C_{14}$ aryl, an unsubstituted or substituted 5- to 10-membered heteroaryl, wherein 1 to 4 ring atoms are independently selected from nitrogen, oxygen or sulfur, an unsubstituted or substituted 5- to 10-membered heteroalicyclic ring, wherein 1 to 3 ring atoms are independently nitrogen, oxygen or sulfur, —OR$^3$, —SR$^3$, —C(O)R$^3$, —C(S)R$^3$, —C(O)OR$^3$, —C(S)OR$^3$, —C(O)NR$^3$R$^4$, —NR$^3$R$^4$, —S(O)$_2$R$^3$, —S(O)$_2$OR$^3$, and —S(O)$_2$NR$^3$R$^4$, —SCF$_3$, —SOCF$_3$ or —SO$_2$CF$_3$, or —OCF$_3$, —CN, —CF$_3$, —SCN, —F, —Cl, —Br or —l, wherein R$^3$ and R$^4$ are independently selected from the group consisting of hydrogen, unsubstituted or substituted $C_1$-$C_4$ alkyl, in particular a unsubstituted $C_1$-$C_4$ alkyl, and $C_1$-$C_4$ alkyl substituted with $C_1$-$C_4$ alkoxy.

In some embodiments, z of $R_z^U$ of the general formula 2b is 0, 1, 2, 3 or 4, and each $R^U$ is independently from any other $R^U$ selected from —OR$^3$, —SR$^3$, —C(O)R$^3$, —C(S)R$^3$, —C(O)OR$^3$, —C(S)OR$^3$, —C(O)SR$^3$, —C(O)NR$^3$R$^4$, —S(O)$_2$R$^3$, —S(O)$_2$OR$^3$, —S(O)$_2$NR$^3$R$^4$, —SCF$_3$, —SOCF$_3$, —SO$_2$CF$_3$, —OCF$_3$, —CN, —CF$_3$, —SCN, —F, —CL, —Br or —l, in particular from —OCF$_3$, —C(O)R$^3$, —C(S)R$^3$ —C(O)OR$^3$, —C(S)OR$^3$, —C(O)SR$^3$, —C(O)NR$^3$R$^4$, —SCF$^3$, —SOCF$_3$ or —SO$_2$CF$_3$, more particularly from —SCF$_3$, —SOCF$_3$ or —SO$_2$CF$_3$, wherein R$^3$ and R$^4$ are independently selected from the group consisting of hydrogen, unsubstituted or substituted $C_1$-$C_4$ alkyl, and $C_1$-$C_4$ alkyl substituted with $C_1$-$C_4$ alkoxy.

In some embodiments, z of $R_z^U$ of the general formula 2b is 1 and $R^U$ is situated on the neighboring carbon atom of the cp-ligand with respect to the attachment position of the organometallic moiety (yielding a 1,2 substitution pattern on the cp-ligand).

In some embodiments, z of $R_z^U$ of the general formula 2b is 1, and $R^U$ is selected from —$OR^3$, —$SR^3$, —$C(O)R^3$, —$C(S)R^3$, —$C(O)OR^3$, —$C(S)OR^3$, —$C(O)SR^3$ —$C(O)NR^3R^4$, —$S(O)_2R^3$, —$S(O)_2OR^3$ —$S(O)_2NR^3R^4$, —$SCF_3$, —$SOCF_3$, —$SO_2CF_3$, —$OCF_3$, —CN, —$CF_3$, —SCN, —F, —Cl, —Br or —I, wherein $R^3$ and $R^4$ are independently selected from the group consisting of hydrogen, unsubstituted or substituted $C_1$-$C_4$ alkyl, and $C_1$-$C_4$ alkyl substituted with $C_1$-$C_4$ alkoxy.

In some embodiments, z of $R_z^U$ of the general formula 2b is 1, and $R^U$ is selected from —$OCF_3$, —$C(O)R^3$, —$C(S)R^3$, —$C(O)OR^3$, —$C(S)OR^3$, —$C(O)SR^3$, —$C(O)NR^3R^4$, —$SCF_3$, —$SOCF_3$ or —$SO_2CF_3$, wherein $R^3$ and $R^4$ are independently selected from the group consisting of hydrogen, unsubstituted $C_1$-$C_4$ alkyl, and $C_1$-$C_4$ alkyl substituted with $C_1$-$C_4$ alkoxy.

In some embodiments, z of $R_z^U$ of the general formula 2b is 1, and $R^U$ is selected from, —$OCF_3$, —$C(O)R^3$, —$C(S)R^3$, —$C(O)OR^3$, —$C(S)OR^3$, —$C(O)SR^3$, —$C(O)NR^3R^4$, —$SCF_3$, —$SOCF_3$ or —$SO_2CF_3$, wherein $R^3$ and $R^4$ are independently selected from the group consisting of hydrogen, unsubstituted $C_1$-$C_4$ alkyl, and $C_1$-$C_4$ alkyl substituted with $C_1$-$C_4$ alkoxy.

In some embodiments, z of $R_z^U$ of the general formula 2b is 1 and $R^U$ is selected from —$OCF_3$, —$SCF_3$, —$SOCF_3$ or —$SO_2CF_3$, in particular from —$SCF_3$, —$SOCF_3$ or —$SO_2CF_3$, wherein $R^3$ and $R^4$ are independently selected from the group consisting of hydrogen, unsunstituted $C_1$-$C_4$ alkyl, and $C_1$-$C_4$ alkyl substituted with $C_1$-$C_4$ alkoxy. In some embodiments, z of $R_z^U$ of the general formula 2b is 1 and $R^U$ is selected from —$OCF_3$, —$SCF_3$, —$SPCF_3$ or —$SO_2CF_3$, in particular from —$SCF_3$, —$SOCF_3$ or —$SO_2CF_3$, wherein in particular $R^U$ is situated on the neighboring carbon atom of the cp-ligand with respect to the attachment position of the organometallic moiety (yielding a 1,2 substitution pattern on the cp-ligand).

In some embodiments, z of $R_z^U$ of the general formula 2b is 0.

In some embodiments, M of the general formula 2b is Mn, Re or Tc, z of $R_z^U$ is 0, i of $F_i$, r of $K_r$ and t of $K_t$ are 0, and $F_l$ is —C(=O)— or —C(=S), with l being 1, q of $K_q$ is 0, p of $K_p$ is 0;

$F_l$ is —C(=O)—, with l being 1, q of $K_q$ is 0, p of $K_p$ is 0;

$F_l$ is —C(=O)— or —C(=S), with l being 1, q of $K_q$ is 0, $K_p$ is $C_1$- or $C_2$-alkyl;

$F_l$ is —C(=O)—, with l being 1, q of $K_q$ is 0, $K_p$ is $C_1$- or $C_2$-alkyl;

$F_l$ is —C(=O)—, with l being 1, p of $K_p$ is 0, $K_q$ is $C_1$- or $C_2$-alkyl;

$F_l$ is —C(=O)—, with l being 1, p of $K_p$ is $C_1$- or $C_2$-alkyl, $K_q$ is $C_1$- or $C_2$-alkyl;

$F_l$ is —C(=O)—, with l being 1, q of $K_q$ is 0, $K_p$ is $C_1$-alkyl;

$F_l$ is —C(=O)—, with l being 1, q of $K_q$ is 0, $K_p$ is $C_2$-alkyl;

$F_l$ is —C(=O)—, with l being 1, p of $K_p$ is 0, $K_q$ $C_1$-alkyl;

$F_1$ is —C(=O)—, with l being 1, p of $K_p$ is 0, $K_q$ $C_2$-alkyl.

In some embodiments, M of the general formula 2b is Mn, Re or Tc, z of $R_z^U$ is 1, i of $F_i$, r of $K_r$ and t of $K_t$ are 0, and $F_l$ is —C(=O)— or —C(=S), with l being 1, q of $K_q$ is 0, p of $K_p$ is 0;

$F_l$ is —C(=O)—, with l being 1, q of $K_q$ is 0, p of $K_p$ is 0;

$F_l$ is —C(=O)— or —C(=S), with l being 1, q of $K_q$ is 0, $K_p$ is $C_1$- or $C_2$-alkyl;

$F_l$ is —C(=O)—, with l being 1, q of $K_q$ is 0, $K_p$ is $C_1$- or $C_2$-alkyl;

$F_l$ is —C(=O)—, with l being 1, p of $K_p$ is 0, $K_q$ is $C_1$- or $C_2$-alkyl;

$F_l$ is —C(=O)—, with l being 1, $K_p$ is $C_1$-alkyl, $K_q$ is $C_2$-alkyl;

$F_l$ is —C(=O)—, with l being 1, q of $K_q$ is 0, $K_p$ is $C_1$-alkyl;

$F_l$ is —C(=O)—, with l being 1, q of $K_q$ is 0, $K_p$ is $C_2$-alkyl, $F_l$ is —C(=O)—, with l being 1, p of $K_p$ is 0, $K_q$ is $C_1$-alkyl;

$F_l$ is —C(=O)—, with l being 1, p of $K_p$ is 0, $K_q$ is $C_2$-alkyl;

wherein in particular $R^U$ is selected from, —$OCF_3$, —$SCF_3$, —$SOCF_3$ or —$SO_2CF_3$, in particular from —$SCF_3$, —$SOCF_3$ or —$SO_2CF_3$, wherein more particularly —$OCF_3$, —$SCF_3$, —$SOCF_3$ or —$SO_2CF_3$, in particular from —$SCF_3$, —$SOCF_3$ or —$SO_2CF_3$, are situated on the neighboring carbon atom of the cp-ligand with respect to the attachment position of the organometallic moiety (yielding a 1,2 substitution pattern on the cp-ligand).

In some embodiments, M of the general formula 2b is Mn, Re or Tc, z of $R_z^U$ is 0, and $F_l$ is —C(=O)— or —C(=S), with l being 1, q of $K_q$ is 0, p of $K_p$ is 0;

$F_l$ is —C(=O)—, with l being 1, q of $K_q$ is 0, p of $K_p$ is 0;

$F_l$ is —C(=O)— or —C(=S), with l being 1, q of $K_q$ is 0, $K_p$ or $C_1$- or $C_2$-alkyl;

$F_l$ is —C(=O)—, with l being 1, q of $K_q$ is 0, $K_p$ is $C_1$- or $C_2$-alkyl;

$F_l$ is —C(=O)—, with l being 1, p of $K_p$ is 0, $K_q$ is $C_1$- or $C_2$-alkyl;

$F_l$ is —C(=O)—, with l being 1, $K_p$ is $C_1$- or $C_2$-alkyl, $K_q$ is $C_1$- or $C_2$-alkyl;

$F_l$ is —C(=O)—, with l being 1, q of $K_q$ is 0, $K_p$ is $C_1$-alkyl;

$F_l$ is —C(=O)—, with l being 1, q of $K_q$ is 0, $K_p$ is $C_2$-alkyl;

$F_l$ is —C(=O)—, with l being 1, p of $K_p$ is 0, $K_q$ is $C_1$-alkyl;

$F_l$ is —C(=O)—, with l being 1, p of $K_p$ is 0, $K_q$ is $C_1$-alkyl.

In some embodiments, M of the general formula 2b is Mn, Re or Tc, z of $R_z^U$ is 1, and $F_l$ is —C(=O)— or —C(=S), with l being 1, q of $K_q$ is 0, p of $K_p$ is 0;

$F_l$ is —C(=O)—, with l being 1, q of $K_q$ is 0, p of $K_p$ is 0;

$F_l$ is —C(=O)— or —C(=S), with l being 1, q of $K_q$ is 0, $K_p$ is $C_1$- or $C_2$-alkyl;

$F_l$ is —C(=O)—, with l being 1, q of $K_q$ is 0, $K_p$ is $C_1$- or $C_2$-alkyl;

$F_1$ is —C(=O)—, with l being 1, p of $K_p$ is 0, $K_q$ is $C_1$- or $C_2$-alkyl;

$F_l$ is —C(=O)—, with l being 1, p of $K_p$ is $C_1$ or $C_2$-alkyl, $K_q$ is $C_1$- or $C_2$-alkyl;

$F_l$ is —C(=O)—, with l being 1, q of $K_q$ is 0, $K_p$ is $C_1$-alkyl;

$F_l$ is —C(=O)—, with l being 1, q of $K_q$ is 0, $K_p$ is $C_2$-alkyl;

$F_l$ is —C(=O)—, with l being 1, p of $K_p$ is 0, $K_q$ is $C_1$-alkyl;

$F_l$ is —C(=O)—, with l being 1, p of $K_p$ is 0, $K_q$ is $C_2$-alkyl.

Wherein in particular $R^U$ is selected from —OCF$_3$, —SCF$_3$, —SOCF$_3$ or —SO$_2$CF$_3$, in particular from —SCF$_3$, —SOCF$_3$ or —SO$_2$CF$_3$, wherein more particularly —OCF$_3$, —SCF$_3$, —SOCF$_3$ or —SO$_2$CF$_3$, in particular from —SCF$_3$, —SOCF$_3$ or —SO$_2$CF$_3$, are situated on the neighboring carbon atom of the cp-ligand with respect to the attachment position of the organometallic moiety (yielding a 1,2 substitution pattern on the cp-ligand).

The half metal sandwich complex of the general formula (2b) in the above mentioned embodiments may be neutral or cationic species, particularly the half metal sandwich complex with M being Co may be in the cationic form comprising a counter anion CA selected from I$^-$, Cl$^-$, Br$^-$, BF$_4{}^-$, CF$_3$SO$_3{}^-$(OTf) or PF$_6{}^-$, In some embodiments, OM is a metal sandwich complex of the general formula (2c),

(2c)

wherein $R^c$ is selected from
hydrogen,
an unsubstituted or substituted $C_1$-$C_{10}$ alkyl, an unsubstituted or substituted $C_1$-$C_{10}$ alkenyl, an unsubstituted or substituted $C_1$-$C_{10}$ alkynyl, an unsubstituted or substituted $C_3$-$C_8$ cycloalkyl, an unsubstituted or substituted $C_1$-$C_{10}$ alkoxy, an unsubstituted or substituted $C_3$-$C_8$ cycloalkoxy,
an unsubstituted or substituted $C_6$-$C_{14}$ aryl,
an unsubstituted or substituted 5- to 10-membered heteroaryl, wherein 1 to 4 ring atoms are independently selected from nitrogen, oxygen or sulfur,
an unsubstituted or substituted 5- to 10-membered heteroalicyclic ring, wherein 1 to 3 ring atoms are independently nitrogen, oxygen or sulfur,
—OCF$_3$, —OR$^3$, —SR$^3$, —C(O)R$^3$, —C(S)R$^3$, —C(O)OR$^3$, —C(S)OR$^3$, —C(O)SR$^3$, —C(O)NR$^3$R$^4$, NR$^3$R$^4$, —S(O)$_2$R$^3$, —S(O)$_2$OR$^3$, and —S(O)$_2$NR$^3$R$^4$,
—SCF$_3$, —SOCF$_3$ or —SO$_2$CF$_3$
wherein
$R^3$ and $R^4$ are independently selected from the group consisting of hydrogen, unsubstituted or substituted $C_1$-$C_4$ alkyl, in particular a $C_1$-$C_4$ alkyl, and $C_1$-$C_4$ alkyl substituted with $C_1$-$C_4$ alkoxy.

In some embodiments, $R^c$ of the general formula 2c is selected from —OCF$_3$, —OR$^3$, —SR$^3$, —C(O)R$^3$, —C(S)R$^3$, —C(O)OR$^3$, —C(S)OR$^3$, —C(O)SR$^3$, —C(O)NR$^3$R$^4$, —S(O)$_2$R$^3$, —S(O)$_2$OR$^3$, —S(O)$_2$NR$^3$R$^4$, —SCF$_3$, —SOCF$_3$ or —SO$_2$CF$_3$, wherein $R^3$ and R$^4$ are independently selected from the group consisting of hydrogen, unsubstituted or substituted $C_1$-$C_4$ alkyl, and $C_1$-$C_4$ alkyl substituted with $C_1$-$C_4$ alkoxy. In some embodiments, $R^c$ of the general formula 2c is selected from —OCF$_3$, —C(O)R$^3$, —C(S)R$^3$, —C(O)OR$^3$, —C(S)OR$^3$, —C(O)SR$^3$, —C(O)NR$^3$R$^4$, —SCF$_3$, —SOCF$_3$ or —SO$_2$CF$_3$, wherein $R^3$ and $R^4$ are independently selected from the group consisting of hydrogen, unsubstituted or substituted $C_1$-$C_4$ alkyl, and $C_1$-$C_4$ alkyl substituted with $C_1$-$C_4$ alkoxy. In some embodiments, $R^c$ of the general formula 2c is selected from —SCF$_3$, —SOCF$_3$ or —SO$_2$CF$_3$, wherein $R^3$ and $R^4$ are independently selected from the group consisting of hydrogen, unsubstituted or substituted $C_1$-$C_4$ alkyl, and $C_1$-$C_4$ alkyl substituted with $C_1$-$C_4$ alkoxy.

In some embodiments, $R^c$ of the general formula 2c is hydrogen.

In some embodiments, $R^c$ of the general formula 2c is an unsubstituted or substituted $C_1$-$C_{10}$ alkyl in particular an unsubstituted $C_1$-$C_4$ alkyl, an unsubstituted or substituted $C_1$-$C_{10}$ alkenyl, an unsubstituted or substituted $C_1$-$C_{10}$ alkynyl, an unsubstituted or substituted $C_3$-$C_8$ cycloalkyl, an unsubstituted or substituted $C_1$-$C_{10}$ alkoxy, an unsubstituted or substituted $C_3$-$C_8$ cycloalkoxy.

Particular embodiments of this aspect of the invention are:

a. N-(1-(ferrocenyloxy)-2-cyanopropan-2-yl)ferroceneamide (1)

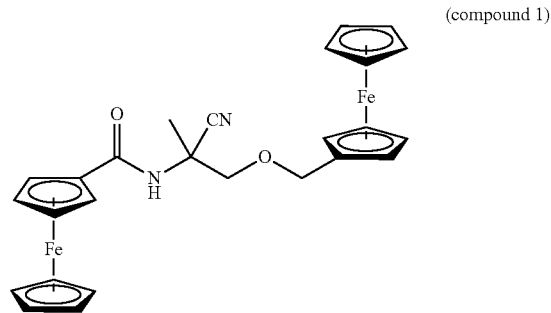

(compound 1)

b. 2-Ferroceneamido-2-cyanopropyl ferrocenate (2)

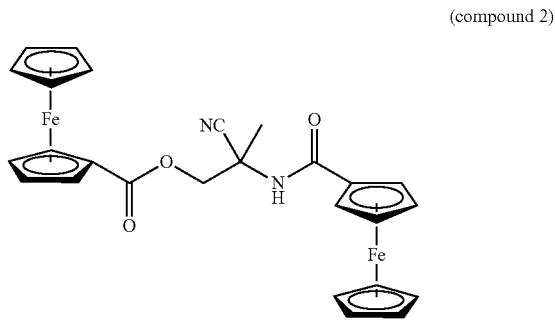

(compound 2)

c. 2-Ferroceneamido-2-cyanopropyl ferrocenate (2a)

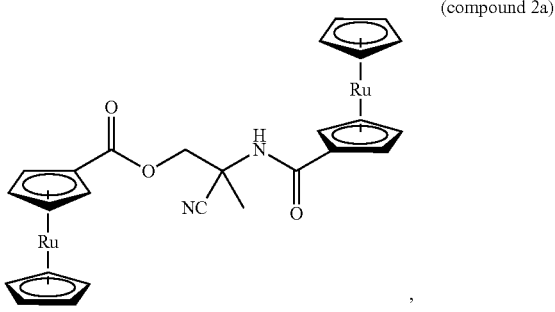

(compound 2a)

The compounds of the general formula (1) can also be obtained in the form of their hydrates and/or also can include other solvents used for example for the crystallization of compounds present in the solid form. Depending on the method and/or the reaction conditions, compounds of the general formula (1) can be obtained in the free form or in the form of salts.

The compounds of the general formula (1) may be present as optical isomers or as mixtures thereof. The stereocenter is marked with an asterisk in the general formulas and is located on the C1 carbon atom of the ethyl moiety, however, the stereocenter is not depicted in all of the formulas of the specific compounds due to simplicity reasons. The invention relates both to the pure isomers, racemic mixtures and all possible isomeric mixtures and is hereinafter understood as doing so, even if stereochemical details are not specifically mentioned in every case. Enantiomeric mixtures of compounds of the general formula (1), which are obtainable by the process or any other way, may be separated in known manner—on the basis of the physical-chemical differences of their components—into pure enantiomers, for example by fractional crystallisation, distillation and/or chromatography, in particular by preparative HPLC using a chiral HPLC column.

According to the invention, apart from separation of corresponding isomer mixtures, generally known methods of diastereoselective or enantioselective synthesis can also be applied to obtain pure diastereoisomers or enantiomers, e.g. by carrying out the method described hereinafter and using educts with correspondingly suitable stereochemistry.

It is advantageous to isolate or synthesise the biologically more active isomer, provided that the individual compounds have different biological activities.

A further object of the invention is the process for the preparation of the compounds described by the general formula (1).

The preparation comprises a compound described by the following general formula

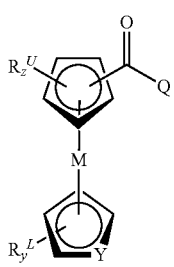

(compound 3)

Compound 3 comprising the substituents $R_y^L$, $R_z^U$, Y, Q, and M as defined above, is a known compound, which can be purchased or may be synthesized by known procedures or may be prepared analogously to known compounds. Such procedures are described by, without being limited to it, Patra et al. (*J. Med. Chem.* 2012, 55, 8790-8798; Apreutesei et al. (*Appl. Organomet. Chem.* 2005, 19, 1022-1037). Bonini et al. (*Eur. J. Org. Chem.* 2002, 543-550); Routaboul et al. (*J. Organomet. Chem.*, 2001, 637, 364-371). Q is a leaving group or OH, in particular Q is a leaving group as described in WO2005/044784 A1. Optionally, a group Z of the general formula —$K_r$—$F_f$—$K_t$— (with the meaning as defined above and as depicted in the general formula 1) may be introduced between then —C=O—Q moiety and the organometal OM of compound 2.

In some embodiments, compound 3' is used instead of compound 3.

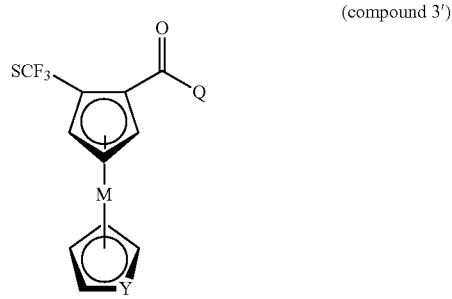

(compound 3')

The reaction pathway is the same as described in Scheme 1 and 2. Compound 3' is producible according to Rhode et. al. (*Synthesis* 2009, 12, 2015-2018 (and references therein)). M, Q and Y have the same meaning as defined above. Optionally, before compound 3' is used the $SCF_3$ moiety may be converted to a $SOCF_3$ or $SO_2SCF_3$ moity via an oxidation according to Trudell et al. (J. Org. Chem. 2003, 68, 5388-5391). Optionally, a group Z of the general formula —$K_r$—$F_f$—$K_t$— (with the meaning as defined above and as depicted in the general formula 1) may be introduced between then —C=o—Q moiety and the organometal OM of compound 3'.

The preparation comprises further a compound described by the following general formula

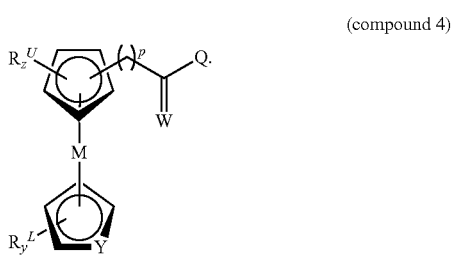

(compound 4)

Compound 4 comprises the substituents $R_y^L$, $R_z^U$, Y, M, Q, p of $K_p$ as defined above. W is O or S. In some embodiments, W is O and Q is Cl and the reaction takes place in the presence of $NEt_3$ In some embodiments, W is O and Q is OH and the reaction takes place in the presence of HATU (O-(7-azabenzotriazol-1-yl)-N,N,N',N'-tetramethyl-uronium-hexafluorophosphate), DIPEA (N,N-Diisopropyl-ethylamine) in N,N-dimethylformamid (comparable to the procedure of Patra et al. (*Organometallics,* 2010, 29, 4312-4319)). Optionally, an alkyl group $K_q$ (with the meaning as defined above) may be introduced between the —C=W moiety (with W being O or S) and the group Q. Compound 4 is a known compound, which can be purchased or may be synthesized by known procedures or may be prepared analogously to known compounds. Such procedures are described for example by Patra et al.(*J. Med. Chem.* 2012, 55, 8790-8798), Apreutesei et al. (*Appl. Organomet. Chem.* 2006, 19, 1022-1037), Bonini et al. (*Eur. J. Org. Chem.* 2002, 543-550); Routaboul et al. (*J. Organomet. Chem.* 2001, 637, 364-371).

The preparation comprises further a compound described by the following general formula

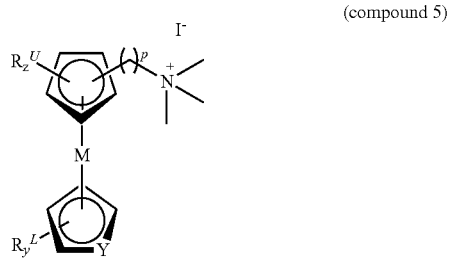

(compound 5)

Compound 5 comprises the substituents $R_y^L$, $R_z^U$, Y, M, p of $K_p$ as defined above. Compound 5 (see scheme 1) is formed by a reaction of the organometallic moity OM of the formula 2a according to a synthetic method similar to the method employed by Gasser et al. (*J. Organomet. Chem.* 2007, 692, 3835-3840).

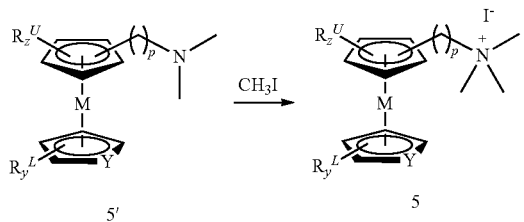

Scheme 1: Formation of compound 5 from compound 5' according to a synthetic method similar to the method employed by Gasser et al. (*J. Organomet. Chem.* 2007, 692, 3835-3840). Compound 5' comprising the substituents $R_y^L$, $R_z^U$, Y, $K_p$ as defined above, is a known compound, which can be purchased or may be synthesized by known procedures or may be prepared analogously to known compounds. Such procedures are described by, without being limited to it, Patra et al. (*J. Med. Chem.* 2012, 8790-8798; Apreutesei et al. (*Appl. Organomet. Chem.* 2005, 19, 1022-1037), Bonini et al. (*Eur. J. Org. Chem.* 2002, 543-550); Routaboul et al. (*J. Organomet. Chem.* 2001, 637, 364-371).

In one embodiment, compound 3 was reacted with compound 6 in the presence of Triethylamine yielding compound 7. The reaction pathway is depicted in scheme 2.

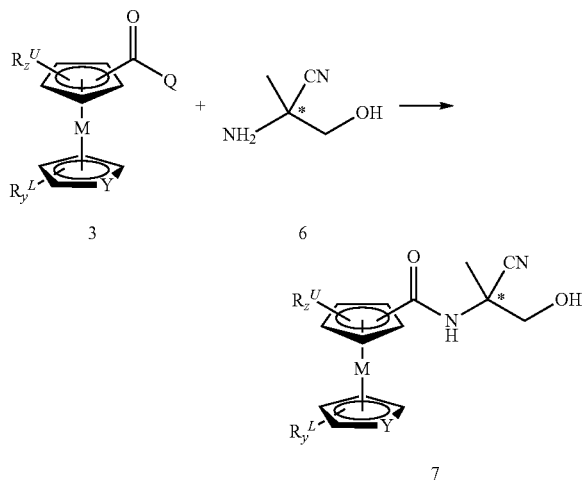

Scheme 2: The 2-amino-2-hydroxymethylproprionitrile derivative 4 was produced according to an adapted procedure according to Gauvry et al. (WO2005/044784A1). $R_y^L$, $R_z^U$, M, Y and Q of compound 3 and 7 have the same meaning as defined above. Compound 3 was reacted with one equivalent of compound 6 yielding compound 7 according to an adapted procedure from Gasser et al. (*J. Organomet. Chem.* 2010, 695, 249-255). In some embodiments, Q is Cl and the reaction takes place in the presence of $NEt_3$. In some embodiments, Q is OH and the reaction takes place in the presence of HATU, DIPEA in N,N-dimethylformamid (comparable to the procedure of Patra et al. (*Organometallics*, 2010, 29, 4312-4319)). In some embodiments, the OH group may be exchanged to the leaving group Cl according to a procedure described by Lorkowski et. al. (VIII. Preparation of monomeric and polymeric ferrocenylene oxadiazoles, *J. Prakt. Chem.* 1967, 35, 149-58), by Witte et al. (*Organometallics* 1999, 18, 4147-4155) or by Cormode et al. (*Dalton Trans.* 2010, 39, 6532-6541=.

In one embodiment, compound 4 was reacted with compound 7, according to an adapted procedure of Gasser et al. (*J. Med. Chem.* 2012, 55, 8790-8798), yielding compound 8a. The reaction pathway is depicted in scheme 3.

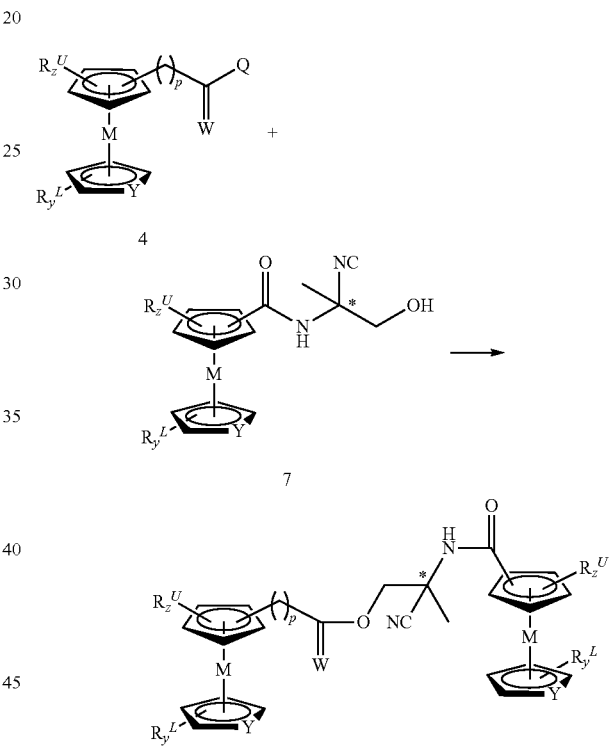

Scheme 3: Compound 4 was reacted with compound 7, according to an adapted procedure of Gasser et al. (*J. Med. Chem.* 2012, 2012, 55, 8790-8798), yielding compound 8a. $R_n^1$, $R_y^L$, $R_z^U$, Y, M, Q, W and p of $K_p$ have the meaning as defined above. In some embodiments, W is O and Q is Cl and the reaction takes place in the presence of $NEt_3$ In some embodiments, W is O and Q is OH and the reaction takes place in the presence of HATU, DIPEA in N,N-dimethylformamid (comparable to the procedure of Patra et al. (*Organometallics*, 2010, 29, 4312-4319)). Optionally, an alkyl group $K_q$ (with the meaning as defined above) may be introduced between then —C=W moiety (with W being O or S) and the group Q. Optionally, a group Z of the general formula —$K_r$—$F_t$—$K_t$— (with the meaning as defined above and as depicted in the general formula 1) may be introduced between then —C=O—Q moiety and the organometal OM of compound 2

In one embodiment, compound 5 was reacted with compound 7, according to an adapted procedure of Gasser et al. (*J. Organomet. Chem.*, 2007, 692, 3835-3840), yielding compound 8b. The reaction pathway is depicted in scheme 4.

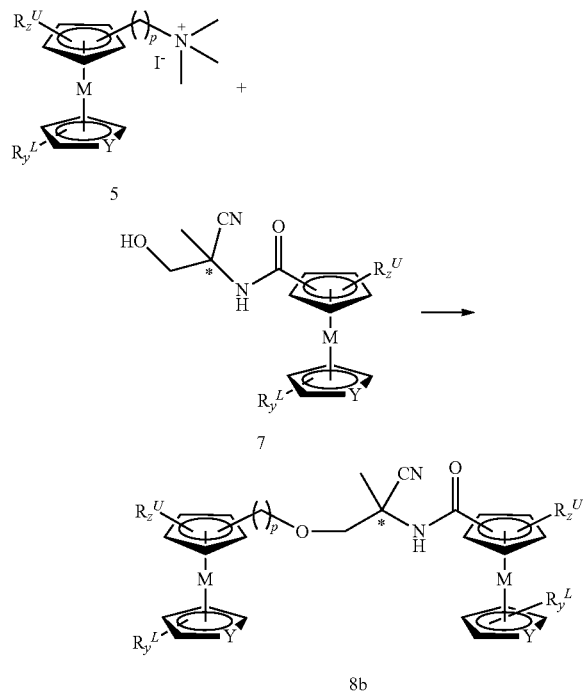

Scheme 4: Compound 5 was reacted with compound 7, according to an adapted procedure of Gasser et al. (*J. Organomet. Chem.* 2007, 692, 3835-3840) and Gasser et al. (*J. Med. Chem.* 2012, 55, 8790-8798). $R_n^1$, $R_y^L$, $R_z^U$, Y and p of $K_p$ have the same meaning as defined above.

In one embodiment, two equivalents of compound 3 were reacted with one equivalent of compound 6 yielding compound 9. The reaction pathway is depicted in scheme 5.

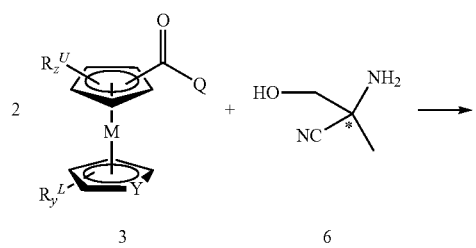

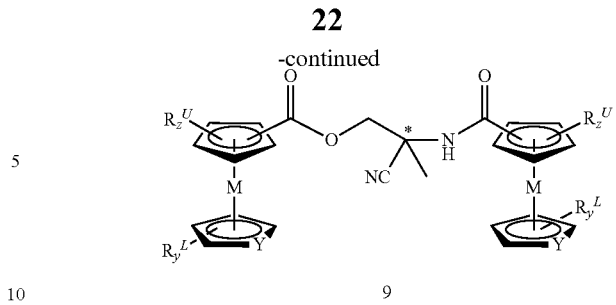

Scheme 5: Two equivalents of compound 3 were reacted with one equivalent of compound 6, according to an adapted procedure from Gasser et al. (*J. Organomet. Chem.* 2010, 695, 249-255), yielding compound 9. $R_y^L$, $R_z^U$, Y, Q and M have the meaning as defined above. In some embodiments Q is a halide, a mesylate or a tosylate. In some embodiments, Q is Cl and the reaction takes place in the presence of $NEt_3$ In some embodiments, Q is OH and the reaction takes place in the presence of HATU, DIPEA in N,N-dimethylformamid (comparable to the procedure of Patra at al. (*Organometallics*, 2010, 29, 4312-4319) or Gasser et al. (*New. J. Chem.* 2012, 36, 1819-1827).

Reaction pathways for compounds comprising the half metal sandwich complexes OM of the general formula 2b follow a similar pathway as the above mentioned reactions, in particular a similar pathway as depicted in scheme 2 to scheme 4, which are easily adaptable for a person skilled in the art. Reference is made to the above cited conditions, references and reactions pathways.

Metal sandwich complex of the general formula (2a) and half metal sandwich complex of the general formula (2b) follow a similar pathway as the above mentioned reactions depicted in scheme 1 and scheme 2, which are easily adaptable for a person skilled in the art. In particular an adaption may be based on publication of Wolter-Steingrube et. al. ("Synthesis and Molecular Structures of Monosubstituted Pentamethylcobaltocenium Cations", Eur. J. Inorg. Chem. 2014, 4115-4122, DOI: 10.1002/ejic.201402443; also Vanicek et al., *Organometalics* 2014, 33, 1152-1156, dx.doi.org/10.1021/om401120h E. Fourie et al., Journal of Organometallic Chemistry 754 (2014) 80e87, dx.doi.org/10.1016/j.korganchem.2013.12.027).

A reaction pathway for compounds comprising carbonyl complexes OM of the general formula 2c is depicted in scheme 6.

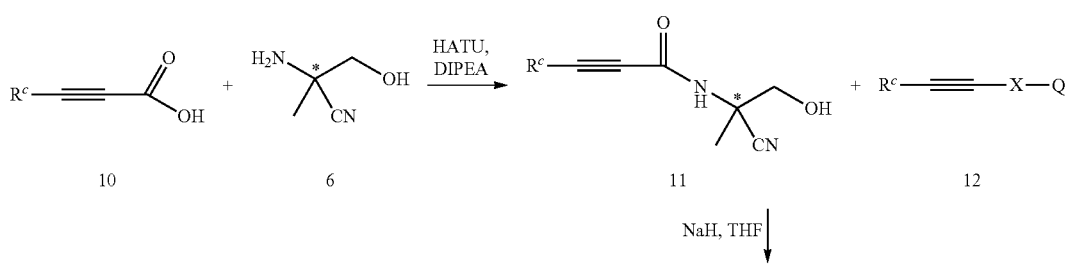

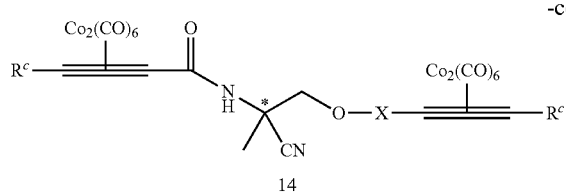
14

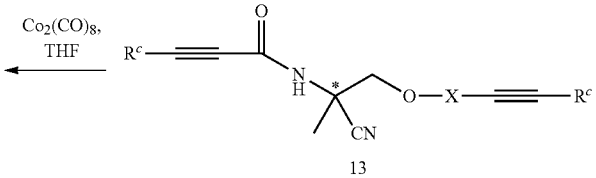
13

Scheme 6: Compound 6 was reacted with compound 10 in the presence of HATU and DIEPA, yielding compound 11 (see Patra at al. (J. Med. Chem. 2012, 55, 8790-8798). X is a group described by a general formula —$K_p$—$F_l$—$K_q$—, as defined above. Furthermore, $R^c$, Q, p, $K_p$, l, $F_l$, q nd $K_q$ have the same meaning as defined above. Compound 11 is then reacted with compound 12 according to an adapted procedure of Gauvry et al. (WO2005/044784A1), yielding compound 13. Subsequently compound 13 is then reacted with 2 equivalents $Co_2(CO)_8$ according to an adapted synthetic method employed by Gasser at al. (INorg. Chem. 2009, 48, 3157-3166), yielding compound 14. Optionally, a group Z of the general formula —$K_r$—$F_f$—$K_t$— (with the meaning as defined above and as depicted in the general formula 1) may be introduced between the —C=O—H moiety and the alkyne moiety of compound 10. Compound 10 and 12 are known compounds, which can be purchased or may be synthesized by known procedures or may be prepared analogously to known compounds (see for example Zeinyeh et al. (Bioorg. Med. Chem. Lett. 2010, 20, 3165-3168).

According to a third aspect of the invention, the compounds defined as the first aspect of the invention are provided for use in a method for treatment of disease.

Pharmaceutically acceptable salts of the compounds provided herein are deemed to be encompassed by the scope of the present invention.

According to one aspect of the invention, a pharmaceutical composition for preventing or treating helminth infection, particularly infection by tapeworms (cestodes), flukes (trematodes) and roundworms (nematodes), in particular species of Haemonchus, Trichstrongylus, Teladorsagia, Cooperia, Oesophagostomum and/or Chabertia, tapeworm infection, schistosomiasis, ascariasis, dracunculiasis, elephantiasis, enterobiasis, filariasis, hookworm infection, onchocerciasis, trichinosis and/or trichuriasis is provided, comprising a compound according to the above aspect or embodiments of the invention.

Pharmaceutical compositions for enteral administration, such as nasal, buccal, rectal or, especially, oral administration, and for parenteral administration, such as dermal (spot-on), intradermal, subcutaneous, intravenous, intrahepatic or intramuscular administration, may be used. The pharmaceutical compositions comprise approximately 1% to approximately 95% active ingredient, preferably from approximately 20% to approximately 90% active ingredient.

According to one aspect of the invention, a dosage form for preventing or treating helminth infection, particularly infection by particularly tapeworms (cestodes), flukes (trematodes) and roundworms (nematodes), tapeworm infection, schistosomiasis, ascariasis, dracunculiasis, elephantiasis, enterobiasis, filariasis, hookworm infection, onchocerciasis, trichinosis and/or trichuriasis is provided, comprising a compound according to the above aspect or embodiments of the invention. Dosage forms may be for administration via various routes, including nasal, buccal, rectal, transdermal or oral administration, or as an inhalation formulation or suppository. Alternatively, dosage forms may be for parenteral administration, such as intravenous, intrahepatic, or especially subcutaneous, or intramuscular injection forms. Optionally, a pharmaceutically acceptable carrier and/or excipient may be present.

According to one aspect of the invention, a method for manufacture of a medicament for preventing or treating helminth infection, particularly infection by particularly tapeworms (cestodes), flukes (trematodes) and roundworms (nematodes), tapeworm infection, schistosomiasis, ascariasis, dracunculiasis, elephantiasis, enterobiasis, filariasis, hookworm infection, onchocerciasis, trichinosis and/or trichuriasisis provided, comprising the use of a compound according to the above aspect or embodiments of the invention. Medicaments according to the invention are manufactured by methods known in the art, especially by conventional mixing, coating, granulating, dissolving or lyophilizing.

According to one aspect of the invention, a method for preventing or treating helminth infection, particularly the indications mentioned previously, is provided, comprising the administration of a compound according to the above aspects or embodiments of the invention to a patient in need thereof.

The treatment may be for prophylactic or therapeutic purposes. For administration, a compound according to the above aspect of the invention is preferably provided in the form of a pharmaceutical preparation comprising the compound in chemically pure form and optionally a pharmaceutically acceptable carrier and optionally adjuvants. The compound is used in an amount effective against helminth infection. The dosage of the compound depends upon the species, the patient age, weight, and individual condition, the individual pharmacokinetic data, mode of administration, and whether the administration is for prophylactic or therapeutic purposes. The daily dose administered ranges from approximately 1 µg/kg to approximately 1000 mg/kg, preferably from approximately 1 µg to approximately 100 µg, of the active agent according to the invention.

Wherever reference is made herein to an embodiment of the invention, and such embodiment only refers to one feature of the invention, it is intended that such embodiment may be combined with any other embodiment referring to a different feature. For example, every embodiment that defines OM may be combined with every embodiment that defines $R_z^U$, $F_l$ or $K_p$, to characterize a group of compounds of the invention or a single compound of the invention with different properties.

The invention is further characterized, without limitations, by the following examples and figure, from with further features, advantages or embodiments can be derived. The examples and figures do not limit but illustrate the invention.

SHORT DESCRIPTION OF THE FIGURES

GENERAL METHODS

Figure 1:
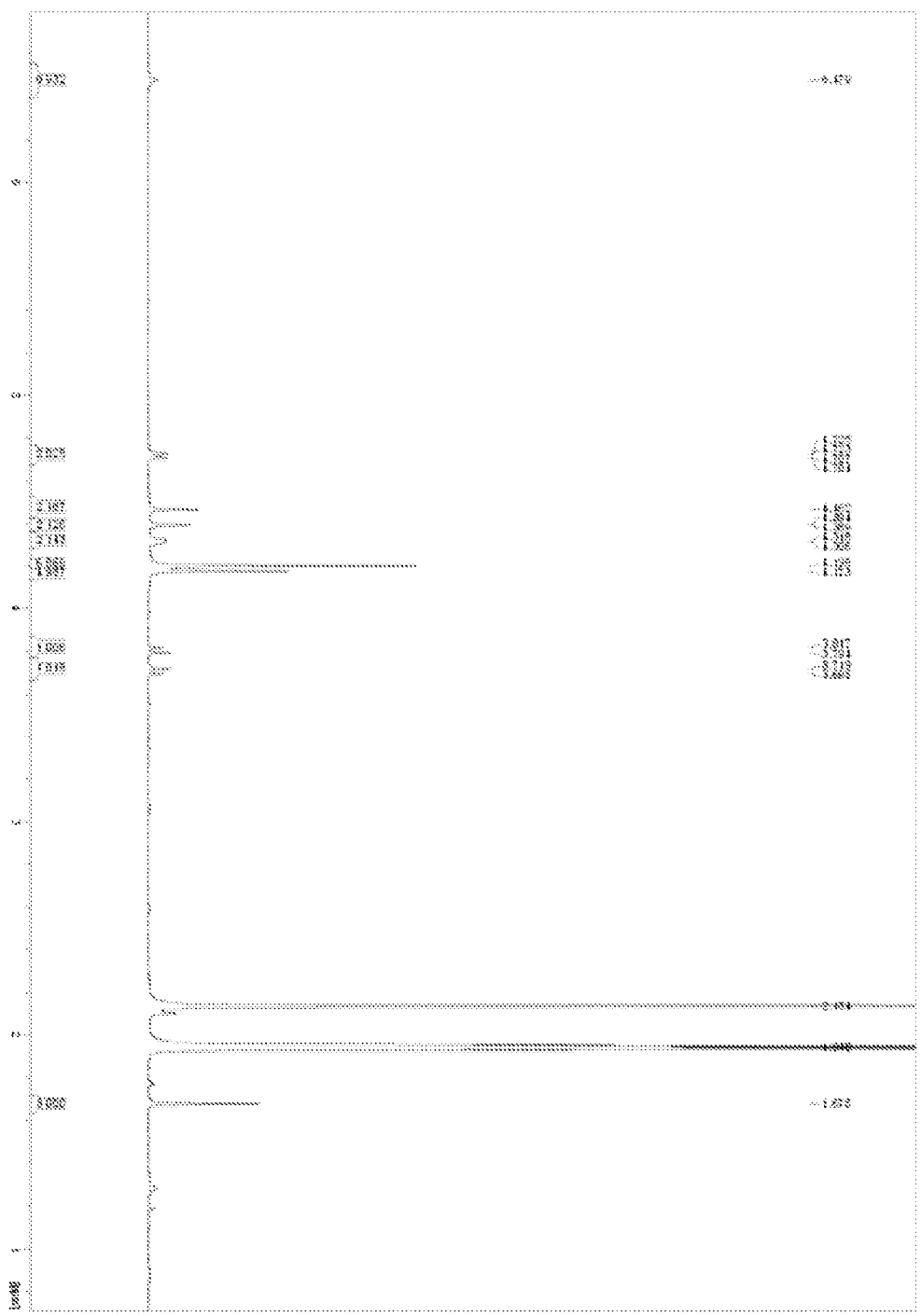
FIG. 1 shows a $^1$H NMR spectrum of Compound 1 in $d_6$-acetonitrile at room temperature.

Materials: All chemicals were of reagent grade quality or better, obtained from commercial suppliers and used without further purification. Solvents were used as received or dried over 4 Å and 3 Å molecular sieves. THF and Et$_2$O were freshly distilled under N$_2$ by employing standard procedures.[57] All syntheses were carried out using standard Schlenk techniques.

Instrumentation and methods: $^1$H- and $^{13}$C-NMR spectra were recorded in deuterated solvents on a Bruker DRX 400 or AV2 500 at 30° C. The chemical shifts δ, are reported in ppm. The residual solvent peaks have been used as internal reference. The abbreviations for the peak multiplicities are as follows: s (singlet), d (doublet), dd (doublet of doublet), t (triplet), q (quartet), m (multiplet) and br (broad). Infrared spectra were recorded on a PerkinElmer spectrum BX TF-IR spectrometer and KBr presslings were used for solids. Signal intensities are abbreviated w (weak), m (medium), s (strong) and br (broad). ESI mass spectra were recorded on a Bruker Esquire 6000 or on a Bruker maxis QTOF-MS instrument (Bruker Daltonics GmbH, Bremen, Germany). The LC-MS spectra were measured on an Acquity™ from Waters system equipped with a PDA detector and an auto sampler using an Agilent Zorbax 300SB-C18 analytical column (5.0 μm particle size, 100 Å pore size, 150×3.0 mm) or an Macherey—Nagel 100—5 C18 (3.5 μm particle size, 300 Å pore size, 150×3.0 mm). This LC was coupled to an Esquire HCT from Bruker (Bremen, Germany) for the MS measurements. The LC run (flow rate: 0.3 mL min-1) was performed with a linear gradient of A (distilled water containing 0.1% v/v formic acid) and B (acetonitrile (Sigma-Aldrich HPLC-grade), t=0 min, 5% B; t=3 min, 5% B; t=17 min, 100% B; t=20 min, 100% B; t=25 min, 5% B. High-resolution ESI mass spectra were recorded on a Bruker maxis QTOF-MS instrument (Bruker Daltonics GmbH, Bremen, Germany). The samples (around 0.5 mg) were dissolved in 0.5 mL of MeCN/H$_2$O 1:1+0.1% HCOOH. The solution was then diluted 10:1 and analysed via continuous flow injection at 3 μL·min$^{-1}$. The mass spectrometer was operated in the positive electrospray ionization mode at 4000 V capillary voltage, −500 V endplate offset, with a N$_2$ nebulizer pressure of 0.4 bar and dry gas flow of 4.0 l/min at 180° C. MS acquisitions were performed in the full scan mode in the mass range from m/z 100 to 2000 at 20'000 resolution and 1 scan per second. Masses were calibrated with a 2 mmol/l solution of sodium formate over m/z 158 to 1450 mass range with an accuracy below 2 ppm.

Cell Culture: Human cervical carcinoma cells (HeLa) were cultured in DMEM (Gibco) supplemented with 5% fetal calf serum (FCS, Gibco), 100 U/ml penicillin, 100 μg/ml streptomycin at 37° C. and 5% CO$_2$. The normal human fetal lung fibroblast MRC-5 cell line was maintained in F-10 medium (Gibco) supplemented with 10% FCS (Gibco), 200 mmol/l L-Glutamine, 100 U/ml penicillin, and 100 μg/ml streptomycin at 37° C. and 5% CO2. To establish the anticancer potential of the compounds they were tested in one cell line, namely HeLa by a fluorometric cell viability assay using Resazurin (Promocell GmbH). Compounds showing cytotoxicity were then tested on normal MRC-5 cells. 1 day before treatment, cells were plated in triplicates in 96-well plates at a density of 4×10$^3$ cells/well in 100μl for HeLa and 7×10$^3$ cells/well for MRC-5 cells. Cells were treated with increasing concentrations of the compounds for 2 days. After 2 days, medium and drug were removed and 100 ml fresh medium containing Resazurin (0.2 mg/ml final concentration) were added. After 4h of incubation at 37° C., the highly red fluorescent dye resorufin's fluorescence was quantified at 590 nm emission with 540 nm excitation wavelength in the SpectraMax M5 microplate Reader.

*C. elegans* movement inhibition assay: Asynchronous N2 *C. elegans* worms (Bristol) were maintained on nematode growth medium (NGM) agar, seeded with a lawn on OP50 *E. coli* as a food-source, according to standard protocol (Maintenance of *C. elegans*; Stiernagle, T., Ed.; WormBook, 2006.). Worms were harvested from NGM plates by washing with M9 buffer (42 mmol/l Na$_2$HPO$_4$, 86 mmol/l NaCl and 1 mmol/l MgSO$_4$), aspiration and collection in a 10 mL tube (Falcon). The average number of worms in 5 μL of this suspension was calculated by transferring 4×5 μL aliquots to a glass slide (Menzel Glaser), and worms were enumerated under a compound microscope (Olympus CH30). To adjust the suspension to contain 1 worm per μL, M9 buffer was either added or removed after pelleting worms at 600×g for 30 sec.

Dilution of test compounds, Zolvix (monepantel) and DMSO for working stock solutions and 96 well plate set-up for liquid screen: A volume of 70 M9 buffer was added to each well in a 96-well plate, using a multichannel pipettor. A volume of 20μL of worm suspension was added to each well using a single-channel pipettor, with a trimmed pipette tip (increased aperture to minimize damage to worms). The worm suspension was resuspended by flicking after every three wells to maintain consistency. The compounds were stored at 4° C., and diluted in dimethyl sulfoxide (DMSO) to achieve a 100 mmol/l concentration 1 hr prior to addition to assay. These stock solutions were diluted further in DMSO to create a series of 20 mmol/l, 2 mmol/l, 0.02 mmol/l and 0.002 mmol/l which were subsequently diluted 1:20 in M9 buffer to create 1 mmol/l, 0.1 mmol/l, 1 μmol/l and 0.1 μmol/l (all 5% (v/v) DMSO). 10 μL of each concentration was added to wells in duplicate to achieve final concentrations of 100 μmol/l, 10 μmol/l, 100 nmol/l and 10 nmol/l in 100 μL (0.5% DMSO). A Zolvix (monepantel) dilution series was simultaneously created following the same dilution schema, and used as a positive control; 10 μL of 10% DMSO was added to achieve 1% DMSO vehicle control. 10 μL M9 was added to negative control wells (see FIG. 1). Plates were incubated at room temperature (22-24° C.) overnight at 20° C.

Quantitative worm mobility scoring: Immobile worms were counted as a percentage of total worms in each well using an Olympus SZ30 dissecting microscope. The immobile fraction was subtracted from the total, and this remainder was divided by the total to give a percentage of live worms per well. Descriptive and inferential statistics were deferred until further replicates are performed.

In vitro experiments can be conducted by testing compounds in a larval development assay. To do this, sheep are infected with infective third-stage larvae (L3) of species of *Haemonchus*, *Trichstrongylus*, *Teledorsagia*, *Cooperia*, *Oesophagostomum* or *Chabertia*. Faeces from these sheep are collected and used for experiments; ~100 g of faeces are crushed homogenized and suspended in ~1000 ml of sugar solution (specific gravity 1.2), put through a 'tea strainer' sieve, and the large undigested food material in the sieve discarded. The sugar solution is then placed into a flat dish and strips of plastic overhead transparency film placed on the surface. The plastic is left for at least 45 minutes to allow the eggs to stick and then removed carefully. The eggs are collected by washing them from the plastic film, with water, into a 50 ml centrifuge tube. The water containing egg suspension eggs is put through a 40 mm sieve to remove further plant material and then centrifuged at 1,000×g for 10 minutes. The supernatant is checked for eggs and then discarded as the majority of eggs are at the bottom of the tube. These eggs are collected in 1 ml of water and diluted to ~200 eggs/20 ml.

1. Each compound is tested at five concentrations: 100, 50, 25, 12.5 and 6.25 mmol/l (i.e. serial 2-fold dilutions starting from 100 mmol/l). Dilutions of each compound (10 ml in total) are performed in 1.5 ml microcentrifuge tubes, 1 ml of molten agar added, the tube vortexed and the agar aliquoted (150 ml) into the wells of a 96-well microtitre plate.
2. DMSO is used in a number of wells as solvent-only controls (negative controls) whilst cydectinis used as a positive control. Concentrations of cydectin used for positive controls for the compound re-testing are: 6.25, 12.5, 25, 50 and 100 mmol/l.
3. ~100 eggs (20 ml) are then added to each well.
4. Plates are then incubated overnight at 27° C.
5. Plates are checked the following morning and afternoon to ensure that most eggs had hatched. Any compounds that appeared to have an ovicidal effect are noted.
6. Following hatching of most eggs, 15 ml of nutritive medium is added to feed the larvae. Nutritive medium is prepared as follows: 1 g of yeast extract is added to 90 ml of 0.85% physiological saline and autoclaved for 20 mins at 121° C. Three milliliters of 10× Earle's balanced salt solution is added to 27 ml of yeast extract solution and the pH of the solution adjusted to 5.4-5.6 by the addition of bicarbonate.
7. Following 7 days additional incubation, the numbers of L3 larvae that had developed in each well is determined.

In vivo experiments can be conducted in sheep monospecifically infected with these parasites (i.e. species of *Haemonchus, Trichstrongylus, Teladorsagia, Cooperia, Oesophagostomum* or *Chabertia*)

ENDO PARASITES

Activity in vitro against *Dirofilaria immitis* (Di) (filarial nematodes).

Freshly harvested and cleaned microfilariae from blood from donor animals are used (dogs for Di). The microfilariae are then distributed in formatted microplates containing the test substances to be evaluated for antiparasitic activity. Each compound is tested by serial dilution in order to determine its minimum effective dose (MED). The plates are incubated for 48 hours at 26° C. and 60% relative humidity (RH). Motility of microfilariae is then recorded to identify possible nematocidal activity. Efficacy is expressed in percent reduced motility as compared to the control and standards.

Activity in vitro against *Haemonchus contortus* & *Trichostrongylus colubriformis* (Gastrointestinal nematodes).

Freshly harvested and cleaned nematode eggs are used to seed a suitably formatted microplate containing the test substances to be evaluated for antiparasitic activity. Each compound is tested by serial dilution in order to determine its MED. The test compounds are diluted in nutritive medium allowing the full development of eggs through to 3rd instar larvae. The plates are incubated for 6 days at 28° C. and 60% relative humidity (RH). Egg-hatching and ensuing larval development are recorded to identify a possible nematocidal activity.

Efficacy is expressed in percent reduced egg hatch, reduced development of L3, or paralysis & death of larvae of all stages.

EXAMPLES OF SYNTHETIC PATHWAYS

Example 1

Synthesis of Compound 1 (N-(1-(ferrocenyloxy)-2-cyanopropan-2-yl)ferroceneamide)

The proposed synthetic pathway is depicted in Scheme 7

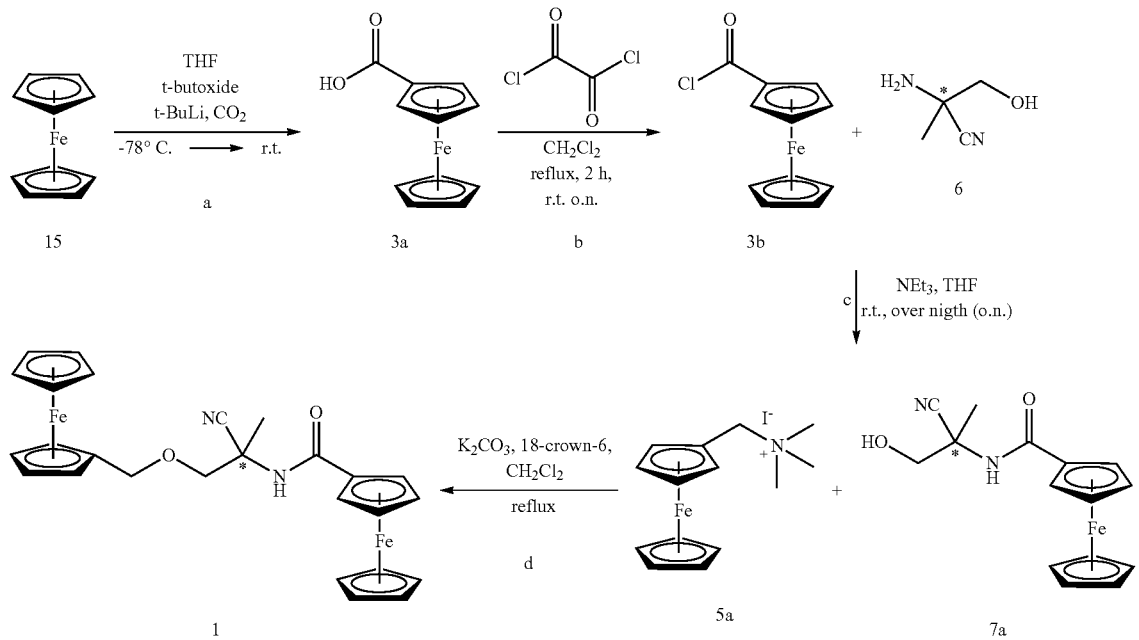

Scheme 7: Reagents and conditions: (a) tert-butoxide, t-BuLi, $CO_2$, THF, $-78°$ C.→r.t., 35%; (b) $CH_2Cl_2$, oxalyl chloride, reflux→r.t., overnight; (c) THF, $NEt_3$, overnight, 29%; (d) $K_2CO_3$ and 18-crown-6, $CH_2Cl_2$, 29%.

Compound 15 was reacted with tert-butoxide, t-BuLi and $CO_2$ yielding compound 3a. The synthesis of ferrocenecarboxylic acid 3a (step a) was adapted from a procedure from Witte et al. (*Organometallics* 1999, 18, 4147). Compound 3a was reacted with oxalyl chloride under reflux yielding compound 3b. The synthesis of chlorocarbonyl ferrocene 3b (step b) was adapted from a procedure of Cormode et al. (*Dalton Trans.*2010, 39, 6532). Optionally an adapted procedure of Lorkowski et. al. (VIII. Preparation of monomeric and polymeric ferrocenylene oxadiazoles, *J. Prakt. Chem.* 1967, 35, 149-58) may be applied. Chlorocarbonyl ferrocene 3b and 2-amino-2-hydroxymethylproprionitrile 6 were dissolved in dry THF and Triethylamine was added (step c). After evaporation of the solvent and purification by column chromatography N-(2-cyano-1-hydroxypropan-2-yl)ferroceneamide 7a was isolated in 29% yield according to an adapted procedure of Gasser et al. (*J. Organomet. Chem.* 2010, 695, 249-255). Compound 7a was reacted with one equivalent of 5a in the presence of $K_2CO_3$ and 18-crown-6 in dry $CH_3CN$ according to an adapted procedure of Gasser et al. (*J. Organomet. Chem.* 2007, 692, 3835-3840) and Gasser et al. (*J. Med. Chem.* 2012, 55, 8790-8798), yielding compound 1 in a yield of 43%.

Example 2

Synthesis Compound 2
(Ferroceneamido-2-cyanopropyl ferrocenate)

The proposed synthetic pathway is depicted in Scheme.8

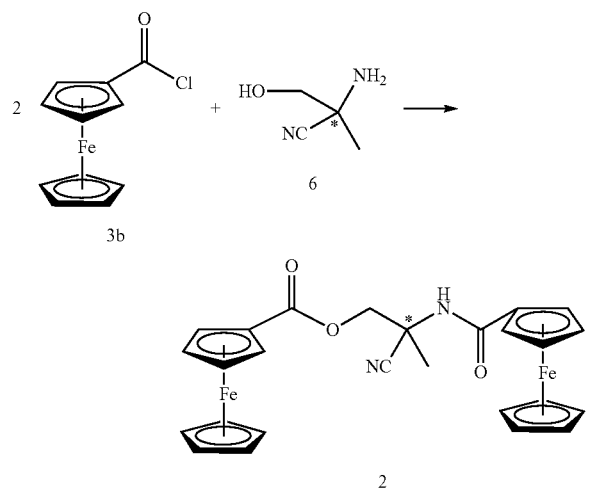

Scheme 8: Two equivalents of Chlorocarbonyl ferrocene 3b and one equivalent of 2-amino-2-hydroxymethylproprionitrile 6 were dissolved in dry THF and Triethylamine was added. After evaporation of the solvent and purification by column chromatography Ferroceneamido-2-cyanopropyl ferrocenate 2 was isolated in: 29% yield. Syntheses and Characterization Ferrocenecarboxylic Acid (3a)

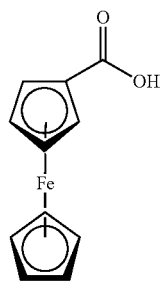

The synthesis of ferrocenecarboxylic acid 3a was adapted from a procedure from Witte et al. (Organometallics, 1999, 18, 4147).

Ferrocene 15 (6.0 g, 32 mmol) and potassium tert-butoxide (0.46 g, 4.08 mmol) were completely dissolved in dry THF (300 mL). The orange solution was cooled to $-78°$ C. when tert-butyllithium (34.0 mL, 64.5 mmol, 1.9 M in pentane) was added dropwise over a period of 15 min, with the temperature maintained below $-70°$ C. The reaction mixture was stirred at $-78°$ C. for 1 h and then poured on a slurry of dry ice (excess) and diethyl ether. The mixture was warmed to room temperature overnight and extracted with an aqueous solution of sodium hydroxide (0.75 N, 4×250 mL). The combined aqueous layers were neutralized with hydrochloric acid (pH>4) and the resulting orange solid was extracted with $Et_2O$ (4×250 mL) until the organic layer remained colourless. The combined organic layers were filtered to remove traces of ferrocenedicarboxylic acid, dried over $MgSO_4$, filtered and the solvent was evaporated under reduced pressure to give ferrocenecarboxylic acid as an orange solid in 35% yield. The spectroscopic data of the product matched that reported previously by Witte et al. (*Organometallics*1999, 18, 4147).

Chlorocarbonyl Ferrocene 3b

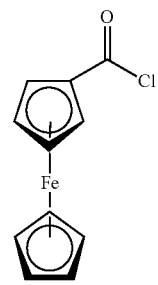

The synthesis of chlorocarbonyl ferrocene 3b was adapted from a procedure of Cormode et al. (*Dalton Trans.*2010, 39, 6532). After suspending ferrocenecarboxylic acid 3a (462 mg, 2.01 mmol) in dry $CH_2Cl_2$ (23 mL), oxalyl chloride (1100 μL, 13.64 mmol) in dry $CH_2Cl_2$ was added dropwise to the reaction mixture whereby the orange suspension turned dark red. The reaction mixture was refluxed for 2 h and then stirred overnight at room temperature. The solvent was then removed under vacuum. The product was not purified and used immediately for the next synthetic step.

2-Amino-2-hydroxymethylproprionitrile 6

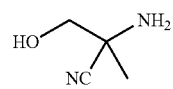

2-Amino-2-hydroxymethylproprionitrile 6 was prepared following the procedure published by Gauvry et al. ((WO2005/044784A1). IR (KBr, cm$^{-1}$): 3329s, 3286s, 3205s, 2985s, 2935s, 2858s, 2756w, 2229m, 1625s, 1476m, 1457m, 1383m, 1368w, 1348w, 1269m, 1178s, 1093s, 1065s, 1044s, 936m, 934s, 888m, 785m, 626w, 465m. $^1$H NMR (400 MHz, MeOD): δ/ppm=3.51 (dd, $^2$J=11.2Hz, $^2$J=10.8 Hz, 2H, CH$_2$), 1.40 (s, 3H, CH$_3$). $^{13}$C NMR (100 MHz, CDCl$_3$): δ/ppm=124.4, 69.8, 53.1, 23.9. ESI-MS: m/z (%)=101.07 ([M+H]$^+$, 100), 83.06 ([M−H$_2$O]$^+$, 64). HR ESI-MS: cald. for C$_4$H$_9$N$_2$O ([M+H]$^+$) m/z (%)=101.07088, found m/z (%)=101.07094.

N-(2-cyano-1-hydroxypropan-2-yl)ferroceneamide 7a

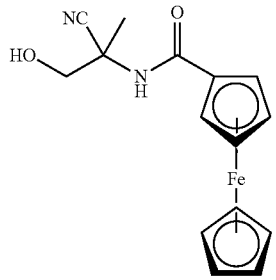

Chlorocarbonyl ferrocene 3b (0.162 g, 0.652 mmol) and 2-amino-2-hydroxymethylproprionitrile 6 (0.065 g, 0.652 mmol) were dissolved in dry THF (15 mL). Triethylamine (453 µL, 3.62 mmol) was added to the solution and the reaction mixture was stirred overnight at room temperature. The solvent was evaporated under reduced pressure and the crude product was purified by column chromatography on silica with hexane:ethyl acetate (7:1→0:1) as the eluent (R$_f$=0.07). The contaminated product was washed with dichloromethane to give N-(2-cyano-1-hydroxypropan-2-yl) ferroceneamide 7a as a pure orange solid. Yield: 29%, IR (KBr, cm$^{-1}$): 3467s, 3412s, 3103w, 2941w, 2862w, 1635s, 1534m, 1454w, 1377w, 1312m, 1267w, 1201w, 1160w, 1099w, 1056m, 1037w, 1023w, 998w, 911w, 826w, 772w, 710w, 620m, 528w, 499w, 483w, 464w. $^1$H NMR (400 MHz, Acetone): δ/ppm=7.12 (s, 1H, NH), 5.01 (t, $^3$=6.4 Hz, 1H, OH), 4.85-4.84 (m, 2H, C$_5$H$_3$), 4.39-4.38 (m, 2H, C$_5$H$_3$), 4,24 (s, 5H, C$_5$H$_5$), 4.0-3.93 (m, 1H, CH$_2$), 3.90-3.86 (m, 1H, CH$_2$), 1.71 (s, 3H, CH$_{3L}$). $^{13}$C NMR (125 MHz, Acetone): δ/ppm=170.9, 121.1, 76.1, 71.5, 70.5, 69.4, 67.0, 66.9, 53.3, 22.6. ESI-MS: m/z (%)=351.02 ([M+K]$^+$, 8), 335.04 ([M+Na]$^+$, 100), 312.06 ([M]$^+$, 52). HR ESI-MS: cald. for C$_{15}$H$_{16}$FeN$_2$O$_2$ (M$^+$) m/z (%)=312.05508, found m/z (%)=312.05557.

(Ferrocenylmethyl)trimethylammonium iodide 5a (Ferrocenylmethyl)trimethylammonium iodide 5a was prepared according to Lindsay et al (*J. Org. Chem.* 1957, 22, 355-358).

N-(1-(ferrocenyloxy-2-cyanopropan-2-yl)ferroceneamide 1

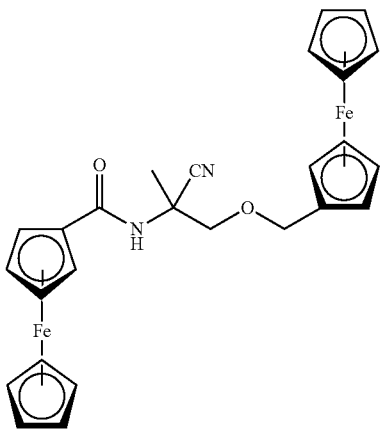

N-(2-cyano-1-hydroxypropan-2-yl)ferroceneamide 7a (0.02 g, 0.064 mmol), (ferrocenylmethyl) trimethylammonium iodide 5a (0.04 g, 0.128 mmol), K$_2$CO$_3$ (26.5 mg, 0.192 mmol) and 18-crown-6 (5.0 mg, 0.0192 mmol) were dissolved in dry CH$_3$CN (10 mL) and refluxed for 72 h. Then the reaction mixture was allowed to cool to room temperature. The solvent was evaporated under reduced pressure. Then the residue was redissolved in CH$_2$Cl$_2$ (10 mL) and washed with H$_2$O (5 mL) and brine (2×5 mL). The organic phase was dried over MgSO$_4$, filtered and the solvent was evaporated under reduced pressure. The crude product was purified by column chromatography on silica with hexane: ethyl acetate (10:1→8:1→3:1→1:1) as the eluent (R$_f$=0.16, (3:1)) to afford N-(1-(ferrocenyloxy)-2-cyanopropan-2-yl) ferroceneamide 1 as a yellow solid. Yield: 43%. IR (KBr, cm$^{-1}$): 3469s, 2929w, 2852w, 1637s, 1518s, 1378w, 1339w, 1305w, 1280w, 1101m, 1008m, 825m, 523m, 502m, 485m. $^1$H NMR (500 MHz, CD$_3$CN): δ/ppm=6.50 (s, 1H, NH), 4.73-4.70 (m, 2H, C$_5$H$_4$), 4.45 (s, 2H, RCH$_2$OR), 4.39-4.38 (m, 2H, C$_5$H$_4$), 4.30 (d, $^3$J=7.7 Hz, 2H, C$_5$H$_4$), 4.19 (s, 7H, C$_5$H$_5$, C$_5$H$_4$), 4.16 (s, 5H, C$_5$H$_5$), 3.80 (d, $^3$J=9.3 Hz, 1H, OCH$_2$CR), 3.70 (d, $^3$J=9.3 Hz, 1H, OCH$_2$CR), 1.67 (s, 3H, CH$_3$). $^{13}$C NMR (125 MHz, CD$_3$CN): δ/ppm=207.9, 171.1, 121.2, 83.8, 75.5, 73.4, 71.9, 70.7, 70.5, 70.4, 69.5, 69.5, 69.4, 69.3, 51.6, 30.1. ESI-MS: m/z (%)=484.03 ([M−CN]$^+$, 12), 510.04 ([M]$^+$, 100), 533.00 ([M+Na]$^+$, 7). HR ESI-MS: cald. for C$_{26}$H$_{26}$Fe$_2$N$_2$O$_2$ ([M+Na]$^+$) m/z (%)=510.06864, found m/z (%)=510.06882.

2-Ferroceneamido-2-cyanopropyl ferrocenate 2

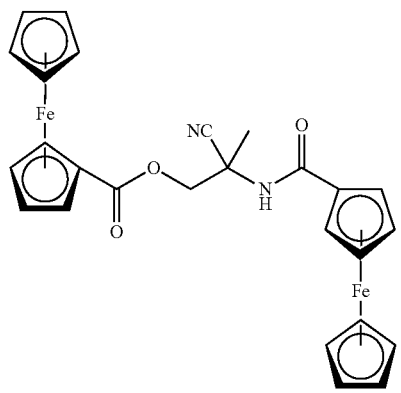

Chlorocarbonyl ferrocene 3b (0.162 g, 0.652 mmol) and 2-amino-2-hydroxymethylproprionitrile 6 (0.065 g, 0.652 mmol) were dissolved in dry THF (15 mL). Triethylamine (453 μL, 3.62 mmol) was added to the solution and the reaction mixture was stirred overnight at room temperature. The solvent was evaporated under reduced pressure and the crude product was purified by column chromatography on silica with hexane:ethyl acetate (7:1→0:1) as the eluent ($R_f$=0.07) to give 2-Ferroceneamido-2-cyanopropyl ferrocenate 2 as a pure orange solid. Yield: 29%. $^1$H NMR (500 MHz, $d_6$-Acetone):δ/ppm=7.53 (s, 1H, NH), 4.88-4.87 (m, 4H, $C_5H_4$), 4.77 (d, $^3J$=11.0 Hz, 1H, $CH_2$), 4.53-4.50 (m, 2H, $C_5H_4$, 1H, $CH_2$), 4.42-4.41 (m, 2H, $C_5H_4$), 4.27 (s, 5H, $C_5H_5$), 4.25 (s, 5H, $C_5H_4$) 1.90 (s, 3H, $CH_3$). $^{13}$C NMR (125 MHz, $d_6$-Acetone):δ/ppm=171.7, 170.7, 120.1, 75.8, 72.7, 71.7, 71.1, 71.0, 70.8, 70.6, 69.5, 69.4, 66.9, 51.5, 23.1. IR (KBr, cm-1): 3467s, 3412s, 3103w, 2941w, 2862w, 1635s, 1534m, 1454w, 1377w, 1312m, 1267w, 1201w, 1160w, 1099w, 1056m, 1037w, 1023w, 998w, 911w, 826w, 772w, 710w, 620w, 528w, 499w, 483w, 464w. ESI-MS: m/z (%)=351.02 ([M+K]+, 8), 335.04 ([M+Na]+, 100), 312.06 ([M]+, 52). HR ESI-MS: cald. for $C_{15}H_{16}FeN_2O_2$(M+) m/z (%)=312.05508, found m/z (%)=312.05557.

N-(2-cyano-1-hydroxypropan-2-yl)ruthenoceneamide (20a) and 2-Cyano-2-(ruthenocenecarboxamido)propyl ruthenocnecarboxylate (2a)

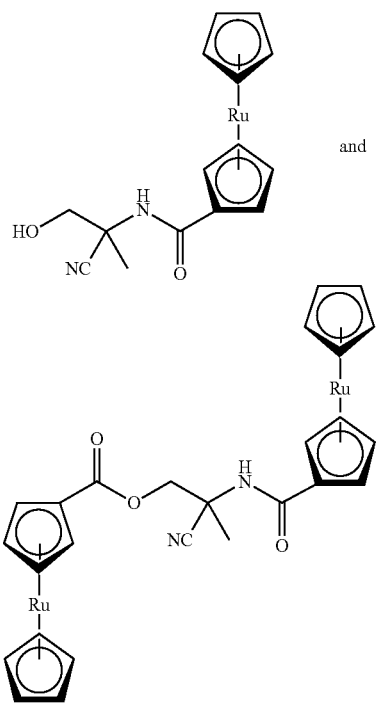

Chlorcarbonyl ruthenocene (1.67 g, 6.96 mmol) and 2-amino-2-hydroxymethyl proprionitrlie (1.05 g, 10.5 mmol) were dissolved in dry THF (50 mL) and NEt3 (6.8 mL, 50 mmol) was slowly added and the mixture was stirred at room temperature for 16 h. The solvent was removed in vacuo and the yellow residue was purified by column chromatography on silica. First, N-(2-cyano-1-hydroxypropan-2-yl)ruthenocenamide 20a was eluted with ethyl acetate:hexane (1:7→7:1) (Rf=0.05 in 1:7 ethyl acetate: hexane) and afterwards 2-cyano-2-(ruthenocenecarboxamido)propyl ruthenocnecarboxylate 2a was eluted with methanol as eluent (Rf=0.2 in methanol) from the same column, both as pale yellow solids. 20a was dissolved in boiling acetonitrile and recrystallized at −4° C. for 4 days. Yield=31%, 20b and 19%, 2a.

N-(2-cyano-1-hydroxypropan-2-yl)ruthenoceneamide (20a): IR (KBr, cm-1): 3248br, 31122s, 3056w, 2943w, 2887w, 2641w, 2324w, 2241w, 2050w, 1981w, 1720w, 1633s, 1531s, 1455s, 1376s, 1308s, 1130s, 823s. 1H NMR (500 MHz, DMSO):δ/ppm=7.49 (s, 1H, NH), 5.63 (t, 3J=6.08 Hz, 1H, OH), 5.22 (s, 2H, C5H4), 4.73 (s, 2H, C5H4), 4.59 (s, 5H, C5H5), 3.78 (dd, 1H, 2J=10.76 Hz, 3J=6.24 Hz, CH2), 3.52 (dd, 1H, 2J=10.76 Hz, 3J=6.08 Hz, CH2), 1.53 (s, 3H, CH3), 13C NMR (500 MHZ, DMSO): δ/ppm=168.2, 120.6, 79.2, 72.5, 71.6, 70.5, 64.9, 52.0, 21.8. ESI-MS: m/z (%)=359.1 ([M+H]+, 100), 259.0 ([M−C4H4N2OH]+, 17). Elemental Analysis: calcd. for C15H16O2N2Ru=C, 50.41; H, 4.51; N, 7.84. Found=C, 50.85; H, 4.44; N, 7.41.

2-Cyano-2-(ruthenocenecarboxamido)propyl ruthenocnecarboxylate (2a): IR (KBr, cm-1): 3320m, 3104w, 2956w, 2651w, 2322w, 2161s, 2053w, 1976s, 1690s, 1656s, 1521s, 1450s, 1373s, 1267s, 1135s, 1035m, 997m, 808s, 759m. 1H NMR (500 MHz, DMSO): δ/ppm=7.96 (s, 1H, NH), 5.28-5.23 (m, 2H, C5H3), 5.16-5.12 (m, 2H, C5H3), 4.84 (t, 3J=1.84 Hz, 2H, $C5H_3$), 4.75 (t, 3J=1.76 Hz, 2H, C5H3), 4.65 (s, 5H, C5H3), 4.59 (s, 5H, C5H3), 4.51 (d, 2J=10.64, 2H, CH2), 4.27 (d, 2J=10.64, 2H, CH2), 1.66 (s, 3H, CH3). 13C NMR (500 MHZ, DMSO): δ/ppm=168.7, 168.3, 119.3, 78.7, 74.1, 73.3, 72.5, 72.0, 71.7, 70.6, 70.4, 64.9, 49.7, 30.7, 22.1. ESI-MS: m/z (%)=639.3 ([M+Na]+, 100).

Elemental Analysis: calcd. for C26H24O3N2Ru2=C, 50.81; H, 3.94; N, 4.56. Found=C, 50.92; H, 3.96; N, 4.53.

Cytotoxicity and Nematocidal Studies:

The toxicity towards human cervical cancer HeLa was investigated using the fluorometric cell viability assay (Resazurin) (Ahmed, S.A.; Gogal, R. M. J.; Walsh, J. E. *J. Immunol. Methods* 1994, 170, 211-224). For compounds which were found to be toxic towards HeLa cells, their cytotoxicity towards the human lung fibroblasts MRC-5 was also tested (see table 1).

*C. elegans* is widely used as a tool in the pharmaceutical and biotechnology industry to test the efficacy of compounds against nematodes and other organisms (cf. Divergence, Inc.—now acquired from the Montsanto Company), which has the major advantage that the modes/mechanisms of action and associated phenotypes can be fully characterised as well as resistance development assessed. Given that *C. elegans* and socioeconomic strongylid nematodes belong to clade V of the phylum Nematoda (Blaxter et al., 1998—*Nature*), there is a high likelihood that drug action will be effective/effected in strongylid nematodes.

TABLE 1 shows the toxicity towards human cervical cancer HeLa and towards the human lung fibroblasts MRC-5 using the fluorometric cell viability assay.

| Compound | $IC_{50}$ in HeLa/μmol/l | $IC_{50}$ in MRC-5/μmol/l |
| --- | --- | --- |
| Compound 2 | >100 | 24.6 |
| Compound 2a | >100 | >100 |

Figure 2:
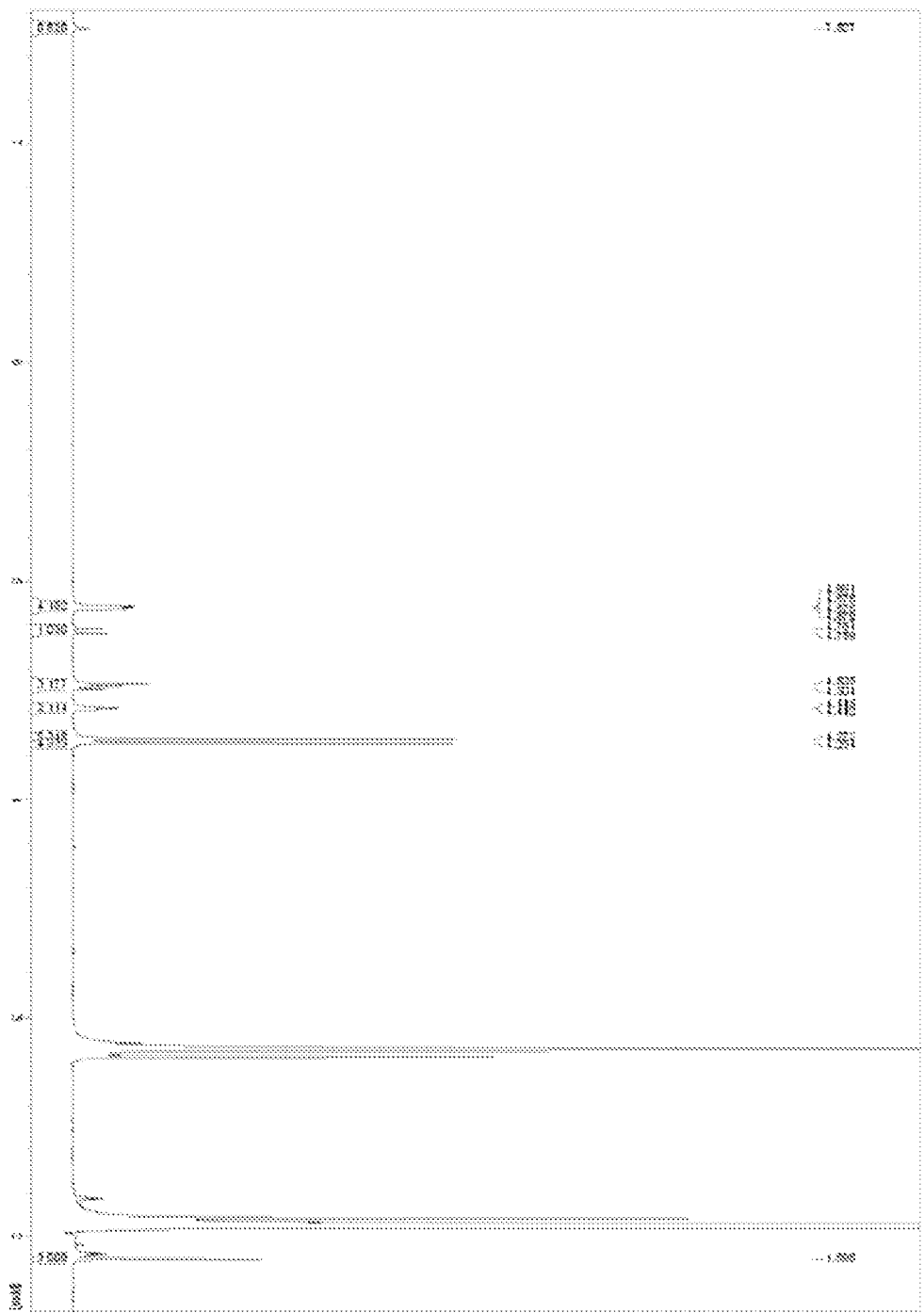
FIG. 2 shows a $^1$H NMR spectrum of Compound 2 in d$_6$-Acetone at room temperature.
Figure 3:
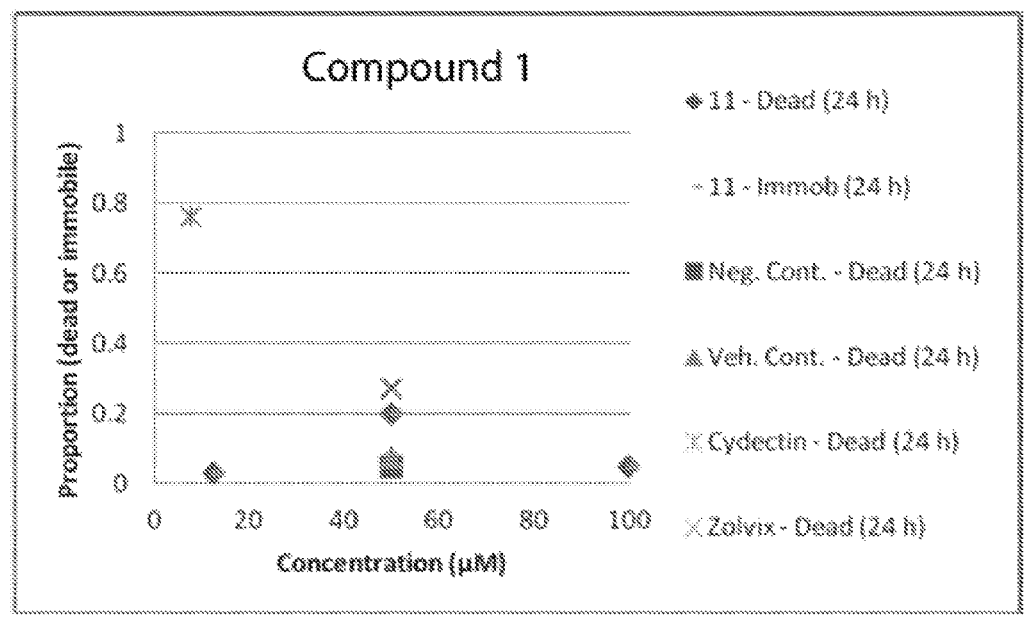
FIG. 3 shows the effect of compound 1 on a *C. elegans* worm suspension (the number of dead or immobile worms after an incubation of 24 h is displayed)
Figure 4:
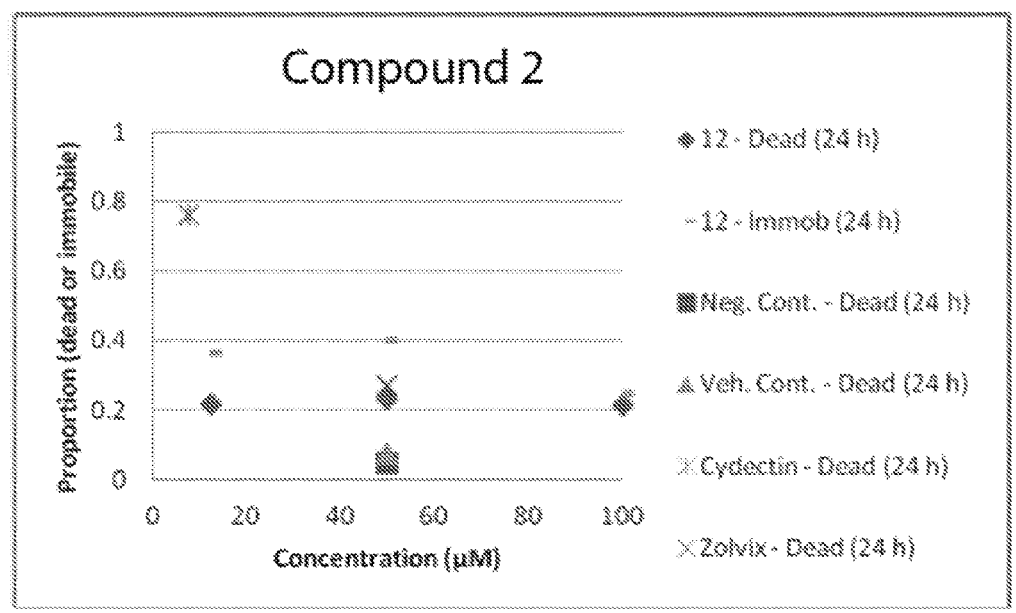
FIG. 4 shows the effect of compound 2 on a *C. elegans* worm suspension (the number of dead or immobile worms after an incubation of 24 h is displayed).

Furthermore, the effect of compound 1 on a *C. elegans* worm suspension is depicted in FIG. 2. The number of dead or immobile worms after an incubation of 24 h is displayed. Table 2 comprises information concerning the effect of compound 1 on *C. elegans* and *H. contortus*. Interestingly, it was demonstrated that the mobility of the *C. elegans* worms was reduced at a concentration of 50 μM indicating a good nematocidal action of compounds 1 and 2.

|  | Mobility in *C. elegans* at 50 μM/% | Number of L3 *H. contortus*/100 μM |
|---|---|---|
| Compound 1 | 25 | 94.7 |
| Compound 2 | 22 | >100 |

The activity against *Haemontus Contortus, Dirofilaria immitis* and *Trychostrongylus colubriformis* was tested and the results are shown in table 3.

TABLE 3 shows the activity against *Haemontus Contortus, Dirofilaria immitis* and *Trychostrongylus colubriformis*

| Compound | Activity against *Haemontus Contortus* at 10 [mg/ml] | Activity against *Dirofilaria immitis* at 10 [mg/ml] | Activity against *Trychostrongylus colubriformis* at 10 [mg/ml] |
|---|---|---|---|
| 1 | 21% | 0% | 17% |
| 2 | 0% | — | 0% |
| 2a | 54% | — | 37% |

As can be seen in Table 3, interesting EC values could be obtained, especially on compound 1 and 2a which had efficacies up to 54% at a dosage of 10 mg/mL. Importantly, since racemic mixtures were used, it can be anticipated that higher activity will be obtain when pure enantiomers will be used.

The invention claimed is:

1. A compound characterized by a general formula (1),

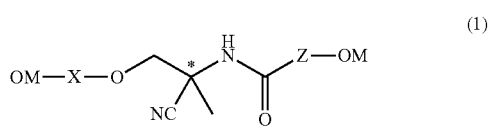

wherein X is a group described by a general formula
—$K_p$—$F_l$—$K_q$—, wherein
$F_l$ is —C(=O)—, —C(=S)—, with l being 0 or 1,
$K_p$ is a $C_p$-alkyl with p being 0, 1, 2, 3 or 4,
$K_q$ is a $C_q$-alkyl with q being 0, 1, 2, 3 or 4, and wherein Z is a group described by a general formula —$K_f$—$F_l$—$K_t$—, wherein
$F_l$ is —O—, —S—, —O—C(=O)—, —O—C(=S)—, —S—C(=O)— or —NH—(C=O)— with i being 0 or 1,
$K_r$ is a $C_r$-alkyl with r being 0, 1, 2, 3 or 4,
$K_t$ is a $C_t$-alkyl with t being 0, 1, 2, 3 or 4,
wherein each OM is an organometallic compound independently selected from each other from the group of an unsubstituted or substituted metal sandwich compound, an unsubstituted or substituted half metal sandwich compound or a metal carbonyl compound.

2. The compound according to claim 1, wherein
l of $F_l$ is 0, q of $K_q$ and p of $K_p$ is 0 or
l of $F_l$ is 0, q of $K_q$ is 0 and $K_p$ is $C_1$-alkyl or
$F_l$ is —C(=O)— with l being 1, q of $K_q$ and p of $K_p$ are 0 or
$F_l$ is —C(=O)— with l being 1, q of $K_q$ is 0 and $K_p$ is $C_1$-alkyl.

3. The compound according to claim 1, wherein l of $F_l$ is 0, r of $K_r$ and t of $K_t$ is 0.

4. The compound according to claim 1, wherein at least one OM is an organometallic compound according to the general formula (2a),

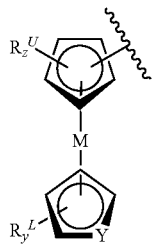

(2a)

wherein M is a metal selected from Fe, Ru, Co, Ni, Cr, Os or Mn, and
Y is C or N, and
z of $R_z^U$ is 0, 1, 2, 3 or 4, and y of $R_y^L$ is 0, 1, 2, 3, 4 or 5 and
each $R^L$ and each $R^U$ are independently from any other $R^L$ and $R^U$ selected from
an unsubstituted or substituted $C_1$-$C_{10}$ alkyl, in particular an unsubstituted $C_1$-$C_4$ alkyl an unsubstituted or substituted $C_1$-$C_{10}$ alkenyl, an unsubstituted or substituted $C_1$-$C_{10}$ alkynyl, an unsubstituted or substituted $C_3$-$C_8$ cycloalkyl, an unsubstituted or substituted $C1$-$C_{10}$ alkoxy, an unsubstituted or substituted $C_3$-$C_8$ cycloalkoxy,
an unsubstituted or substituted $C_6$-$C_{14}$ aryl,
an unsubstituted or substituted 5- to 10-membered heteroaryl, wherein 1 to 4 ring atoms are independently selected from nitrogen, oxygen or sulfur,
an unsubstituted or substituted 5- to 10-membered heteroalicyclic ring, wherein 1 to 3 ring atoms are independently nitrogen, oxygen or sulfur,
—$SCF_3$, —$SOCF_3$ or —$SO_2CF_3$, or
—$OR^3$, —$SR^3$, —C(O)$R^3$, —C(S)$R^3$—C(O)$OR^3$, —C(S)$OR^3$, —C(O)$SR^3$, —C(O)$NR^3R^4$, —$NR^3R^4$, —S(O)$_2R^3$, —S(O)$_2OR^3$ or —S(O)$_2NR^3R^4$, or
—$OCF_3$, —CN, —$CF_3$, —SCN, —F, —Cl, —Br or —I,
wherein $R^3$ and $R^4$ are independently selected from the group consisting of hydrogen, unsubstituted or substituted $C_1$-$C_4$ alkyl, and $C_1$-$C_4$ alkyl substituted with $C_1$-$C_4$ alkoxy.

5. The compound according to claim 4, wherein each $R^L$ and each $R^U$ are independently from any other $R^L$ and $R^U$ selected from
—$OCF_3$, —$OR^3$, —$SR^3$, —C(O)$R^3$, —C(S)$R^3$—C(O)$OR^3$, —C(S)$OR^3$—C(O)$SR^3$, —C(O)$NR^3R^4$, —$NR^3R^4$, —S(O)$_2R^3$, —S(O)$_2OR^3$, —S(O)$_2NR^3R^4$, —$SCF_3$, —$SOCF_3$ or —$SO_2CF_3$, particularly from —$OCF_3$, —C(O)$R^3$, —C(S)$R^3$—C(O)$OR^3$, —C(S)$OR^3$, —C(O)$SR^3$, —C(O)$NR^3R^4$, —$SCF_3$, —$SOCF_3$ or —$SO_2CF_3$,
wherein $R^3$ and $R^4$ are independently selected from the group consisting of hydrogen, unsubstituted or substituted $C_1$-$C_4$ alkyl, and $C1$-$C_4$ alkyl substituted with $C_1$-$C_4$ alkoxy.

6. The compound according to claim 4, wherein each $R^L$ and each $R^U$ are independently from any other $R^L$ and $R^U$ selected from —$SCF_3$, —$SOCF_3$ or —$SO_2CF_3$.

7. The compound according to claim 4, wherein M is selected from the group of Fe, Ru or Co, wherein in particular M is Fe or Ru, and wherein more particularly M is Fe.

8. The compound according to claim 4, wherein Y is C.

9. The compound according to claim 4, wherein y and z are 0.

10. The compound according to claim 1, wherein at least one OM is an organometallic compound according to the general formula (2b),

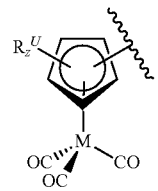

(2b)

wherein M is a metal selected from the group of Mn, Re or Tc, and
z of $R_z^U$ is 0, 1, 2, 3 or 4, and
each $R^U$ is independently from any other $R^U$ selected from
an unsubstituted or substituted $C_1$-$C_{10}$ alkyl, an unsubstituted or substituted $C_1$-$C_{10}$ alkenyl, an unsubstituted or substituted $C_1$-$C_{10}$ alkynyl, an unsubstituted or substituted $C_3$-$C_8$ cycloalkyl, an unsubstituted or substituted $C_1$-$C_{10}$ alkoxy an unsubstituted or substituted $C_3$-$C_8$ cycloalkoxy,
an unsubstituted or substituted $C_6$-$C_{14}$ aryl,
an unsubstituted or substituted 5- to 10-membered heteroaryl, wherein 1 to 4 ring atoms are independently selected from nitrogen, oxygen or sulfur,
an unsubstituted or substituted 5- to 10-membered heteroalicyclic ring, wherein 1 to 3 ring atoms are independently nitrogen, oxygen or sulfur,
—$SCF_3$, —$SOCF_3$ or —$SO_2CF_3$, or
—$OR^3$, —$SR^3$, —C(O)$R^3$, —C(S)$R^3$, —C(O)$OR^3$, —C(S)$OR^3$, —C(O)$SR^3$, —C(O)$NR^3R^4$, —$NR^3R^4$, —S(O)$_2R^3$, —S(O)$_2OR^3$, or —S(O)$_2NR^3R^4$, or
—$OCF_3$, —CN, —$CF_3$, —SCN, —F, —Cl, —Br or —I
wherein $R^3$ and $R^4$ are independently selected from the group consisting of hydrogen, unsubstituted or substituted $C_1$-$C_4$ alkyl, and $C_1$-$C_4$ alkyl substituted with $C_1$-$C_4$ alkoxy.

11. The compound according to claim 10, wherein each $R^U$ is independently from any other $R^U$ selected from
—$OCF_3$, —$OR^3$, —$SR^3$, —$C(O)R^3$, —$C(S)R^3$—$C(O)OR^3$, —$C(S)OR^3$, —$C(O)SR^3$, —$C(O)NR^3R^4$, —$NR^3R^4$, —$S(O)_2R^3$, —$S(O)_2OR^3$, —$S(O)_2NR^3R^4$, —$SCF_3$, —$SOCF_3$ or —$SO_2CF_3$, particularly from —$OCF_3$, —$C(O)R^3$, —$C(S)R^3$, —$C(O)OR^3$, —$C(S)OR^3$, —$C(O)SR^3$, —$C(O)NR^3R^4$, —$SCF_3$, —$SOCF_3$ or —$SO_2CF_3$, more particularly from —$SCF_3$, —$SOCF_3$ or —$SO_2CF_3$, wherein $R^3$ and $R^4$ are independently selected from the group consisting of hydrogen, unsubstituted or substituted $C_1$-$C_4$ alkyl, and $C_1$-$C_4$ alkyl substituted with $C_1$-$C_4$ alkoxy.

12. The compound to claim 1, wherein at least one OM is an organometallic compound according to the general formula (2c),

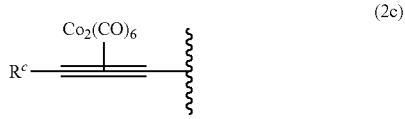

(2c)

wherein $R^c$ is selected from
hydrogen,
an unsubstituted or substituted $C_1$-$C_{10}$ alkyl, in particular an unsubstituted or substituted $C_1$-$C_4$ alkyl, an unsubstituted or substituted $C_1$-$C_{10}$ alkenyl, an unsubstituted or substituted $C_1$-$C_{10}$ alkynyl, an unsubstituted or substituted $C_3$-$C_8$ cycloalkyl, an unsubstituted or substituted $C_1$-$C_{10}$ alkoxy, an unsubstituted or substituted $C_3$-$C_8$ cycloalkoxy,
an unsubstituted or substituted $C_6$-$C_{14}$ aryl,
an unsubstituted or substituted 5- to 10-membered heteroaryl, wherein 1 to 4 ring atoms are independently selected from nitrogen, oxygen or sulfur, an unsubstituted or substituted 5- to 10-membered heteroalicyclic ring, wherein 1 to 3 ring atoms are independently nitrogen, oxygen or sulfur,
—$SCF_3$, —$SOCF_3$ or —$SO_2CF_3$, or
—$OCF_3$, —$OR^3$, —$SR^3$, —$C(O)R^3$, —$C(S)R^3$, —$C(O)OR^3$, —$C(S)OR^3$, —$C(O)SR^3$, —$C(O)NR^3R^4$, —$NR^3R^4$, —$S(O)_2R^3$, —$S(O)_2OR^3$ or —$S(O)_2NR^3R^4$, wherein $R^3$ and $R^4$ are independently selected from the group consisting of hydrogen, unsubstituted $C_1$-$C_4$ alkyl, and $C_1$-$C_4$ alkyl substituted with $C_1$-$C_4$ alkoxy.

13. The compound according to claim 12, wherein $R^c$ is selected from
—$OCF_3$, —$OR^3$, —$SR^3$, —$C(O)R^3$, —$C(S)R^3$—$C(O)OR^3$, —$C(S)OR^3$, —$C(O)SR^3$, —$C(O)NR^3R^4$, —$NR^3R^4$, —$S(O)_2R^3$, —$S(O)_2OR^3$, —$S(O)_2NR^3R^4$, —$SCF_3$, —$SOCF_3$ or —$SO_2CF_3$, particularly from —$OCF_3$, —$C(O)R^3$, —$C(S)R^3$, —$C(O)OR^3$, —$C(S)OR^3$, —$C(O)SRS$, —$C(O)NR^3R^4$, —$SCF_3$, —$SOCF_3$ or —$SO_2CF_3$, more particularly from —$SCF_3$, —$SOCF_3$ or —$SO_2CF_3$, wherein $R^3$ and $R^4$ are independently selected from the group consisting of hydrogen, unsubstituted or substituted $C_1$-$C_4$ alkyl, and $C_1$-$C_4$ alkyl substituted with $C_1$-$C_4$ alkoxy.

14. The compound according to claim 1, wherein each of the two OM are selected independently from each other from compounds comprising the general formula 2a, 2b or 2c, wherein in particular both OM are selected from compounds of the general formula 2a or from compounds of the general formula 2b or from compounds of the general formula 2c.

15. The compound according to claim 1, wherein both OM are the same.

16. A compound according to claim 1 for use in a method of treatment of disease.

17. A compound according to claim 1 for use in a method for treatment of infections by helminths,
or for use in a method to suppress plant helminths.

* * * * *